(12) United States Patent
Heusser

(10) Patent No.: US 12,224,055 B2
(45) Date of Patent: Feb. 11, 2025

(54) SYSTEM AND METHOD FOR ADAPTIVE CONFIGURATION OF COMPUTERIZED COGNITIVE TRAINING PROGRAMS

(71) Applicant: Akili Interactive Labs, Inc., Boston, MA (US)

(72) Inventor: Andrew C. Heusser, Newburyport, MA (US)

(73) Assignee: Akili Interactive Labs, Inc., Boston, MA (US)

( * ) Notice: Subject to any disclaimer, the term of this patent is extended or adjusted under 35 U.S.C. 154(b) by 610 days.

(21) Appl. No.: 17/351,036

(22) Filed: Jun. 17, 2021

(65) Prior Publication Data

US 2022/0406439 A1 Dec. 22, 2022

(51) Int. Cl.
*G16H 20/70* (2018.01)
*A61B 5/16* (2006.01)
(Continued)

(52) U.S. Cl.
CPC ............ *G16H 20/70* (2018.01); *A61B 5/16* (2013.01); *G06N 5/04* (2013.01); *G09B 19/00* (2013.01);
(Continued)

(58) Field of Classification Search
CPC ........ G16H 50/20; G16H 50/00; G16H 20/00; G16H 20/70; G16H 50/30; G16H 80/00; G16H 15/00; G16H 10/20
See application file for complete search history.

(56) References Cited

U.S. PATENT DOCUMENTS 6,678,692 B1 1/2004 Hyatt
7,389,288 B2 6/2008 Chickering et al.
(Continued)

FOREIGN PATENT DOCUMENTS

WO 2008109508 A2 9/2008
WO 2015179522 A1 11/2015
(Continued)

OTHER PUBLICATIONS

Carelli, Laura, et al. "Brain-computer interface for clinical purposes: cognitive assessment and rehabilitation." BioMed research international 2017 (2017). (Year: 2017).*
(Continued)

*Primary Examiner* — Jason B Dunham
*Assistant Examiner* — Constantine Siozopoulos
(74) *Attorney, Agent, or Firm* — Gregory Finch; Finch Paolino, LLC

(57) ABSTRACT

A system, method, and computer platform product for an adaptive cognitive training platform. In accordance with various aspects of the present disclosure, an adaptive cognitive training platform is configured to process user activity data from one or more instances of a computerized cognitive training program to determine a baseline cognitive assessment for one or more cognitive abilities/skills of a user. The cognitive assessment model may be configured to further process the user activity data to predict a relative value or measure of efficacy for one or more computerized stimuli or interactions within the computerized cognitive training program. The adaptive cognitive training platform may be configured to configure, modify and/or present one or more graphical user interface elements for one or more subsequent instances of the computerized cognitive training program according to the predicted value or measure of efficacy of one or more cognitive training tasks.

20 Claims, 18 Drawing Sheets

(51) Int. Cl.
  *G06N 5/04* (2023.01)
  *G09B 19/00* (2006.01)
  *G16H 40/67* (2018.01)
  *G16H 50/20* (2018.01)
  *G16H 50/70* (2018.01)
  *G06F 3/0481* (2022.01)

(52) U.S. Cl.
  CPC ............ *G16H 40/67* (2018.01); *G16H 50/20* (2018.01); *G16H 50/70* (2018.01); *G06F 3/0481* (2013.01)

(56) References Cited

U.S. PATENT DOCUMENTS

| | | |
|---|---|---|
| 8,538,778 B2 | 9/2013 | Neville |
| 9,558,452 B2 | 1/2017 | Guiver et al. |
| 9,672,193 B2 | 6/2017 | Macaro et al. |
| 10,853,520 B2 | 12/2020 | Wille |
| 10,874,355 B2 | 12/2020 | Vaughan et al. |
| 2003/0129574 A1 | 7/2003 | Ferriol et al. |
| 2010/0204920 A1 | 8/2010 | Dranitsaris et al. |
| 2014/0227670 A1 | 8/2014 | Sternberg et al. |
| 2014/0279746 A1 | 9/2014 | De Bruin et al. |
| 2018/0286272 A1 | 10/2018 | McDermott et al. |
| 2020/0008725 A1* | 1/2020 | Bach .................. A61B 5/16 |
| 2020/0380882 A1 | 12/2020 | Alailima et al. |
| 2020/0402643 A1 | 12/2020 | Trees et al. |
| 2021/0161430 A1 | 6/2021 | Mirelman et al. |

FOREIGN PATENT DOCUMENTS

| | | | |
|---|---|---|---|
| WO | WO-2016145372 A1 * | 9/2016 | ............ A61B 5/162 |
| WO | 2018039610 A1 | 3/2018 | |
| WO | 2018081134 A1 | 5/2018 | |
| WO | 2018132483 A1 | 7/2018 | |
| WO | 2018148365 A1 | 8/2018 | |
| WO | 2020081609 A1 | 4/2020 | |
| WO | 2020223033 A3 | 11/2020 | |

OTHER PUBLICATIONS

International Search Report, International application No. PCT/US22/33736. Date of mailing: Sep. 21, 2022. ISA/US, Alexandria, VA.

Written Opinion of the International Searching Authority, International application No. PCT/US22/33736. Date of mailing: Sep. 21, 2022. ISA/US, Alexandria, VA.

* cited by examiner

SYSTEM AND METHOD FOR ADAPTIVE CONFIGURATION OF COMPUTERIZED COGNITIVE TRAINING PROGRAMS

FIELD

The present disclosure relates to the field of interactive computer programs; in particular, systems and methods for adaptive configuration of user interfaces and program instances in computerized cognitive training systems.

BACKGROUND

Computerized cognitive training has emerged as a promising approach toward improving cognition and/or preventing cognitive decline. Computerized cognitive training methods have the benefits of being non-invasive, deliverable in multiple formats, and applicable across a range of participant demographics. Additionally, emerging evidence suggests that targeted cognitive training paradigms can have robust cognitive improvements in specific patient populations. However, the general applicability of computerized cognitive training approaches has been limited by the technical problem of low efficiency and varying degrees of efficacy during the course of a cognitive training regimen.

Prior art solutions have attempted to address the problems associated with efficiency and efficacy of cognitive training methods through various approaches to personalization of computerized cognitive training programs. For example, U.S. Pat. No. 10,559,221 to Martucci et al. provides for a processor-implemented method for enhancing cognitive abilities of a user by personalizing cognitive training regimens through difficulty progression, including performing a cognitive assessment of a user using a set of assessment tasks; estimating a maximal performance of the user related to the set of assessment tasks; determining a performance range based at least in part on the maximal performance of the user; dividing the performance range into a plurality of progress gates, the plurality of progress gates corresponding to a plurality of task difficulty levels; selecting a first progress gate within the performance range; generating a first set of training tasks associated with the first progress gate; and collecting the user's first training responses to the first set of training tasks. Another such prior art solution includes WIPO Pub. No. WO 2009/049404 A1 to Stephane Bergeron, which describes a method and system to optimize cognitive training in single individuals that employs computerized algorithms to tailor a task's difficulty level during its execution to achieve optimal training range for people with widely distributed baselines and/or with fluctuating levels of performance. While such solutions provide teachings and suggestions for personalizing cognitive training through adaptive difficulty of tasks, such solutions fail to suggest meaningful approaches for personalization of computerized cognitive training regimens as a whole.

Other prior art solutions have been proposed for providing adaptive presentation of training tasks/content according to a measured cognitive state of a participant. For example, US Publication No. 20160203726A1 to Hibbs et al. provides for a system and method for improving student learning includes learning material that is presented to a student and a device that is used to acquire physiological data from the student in real time during a learning session. A cognitive assessment algorithm determines a cognitive state of the student using the physiological data, and a learning action algorithm modifies the presentation of the learning material in response to the student's cognitive state. However, such solutions fail to suggest meaningful approaches for predicting participant response within the context of computerized cognitive training regimens.

Certain prior art solutions have been proposed approaches for predicting the efficacy of a course of treatment for a patient. For example, U.S. Pat. No. 8,655,817 to Hasey et al. provides for a medical digital expert system to predict a patient's response to a variety of treatments (using pre-treatment information). The system utilizes data fusion, advanced signal/information processing and machine learning/inference methodologies and technologies to integrate and explore diverse sets of attributes, parameters and information that are available to select the optimal treatment choice for an individual or for a subset of individuals suffering from any illness or disease including psychiatric, mental or neurological disorders and illnesses. The methodology and system can also be used to determine or confirm medical diagnosis, estimate the level, index, severity or critical medical parameters of the illness or condition, or provide a list of likely diagnoses for an individual suffering/experiencing any illness, disorder or condition. However, such solutions fail to suggest meaningful approaches for adaptive personalization of treatment regimens to optimize treatment efficacy through predictive modification of therapeutic interactions.

Through applied effort, ingenuity, and innovation, Applicant has identified deficiencies of prior art solutions and has developed a solution that is embodied by the present disclosure, which is described in detail below.

SUMMARY

In order to provide a basic understanding of the invention, the following is a simplified summary of certain embodiments thereof. This summary is not extensive and is not intended to identify key/critical elements of the invention or to delineate the scope of the invention. Its sole purpose is to present embodiments of the invention in a simplified form as a prelude to the more detailed description that is further below.

Certain aspects of the present disclosure provide for a method for configuring a user interface within a computerized cognitive training regimen, comprising: presenting, with a processor communicably engaged with a computing device, one or more instances of the cognitive training regimen to a user, the cognitive training regimen comprising one or more computerized cognitive training tasks presented via a graphical user interface, wherein the one or more computerized cognitive training tasks are configured to target one or more cognitive abilities of the user; receiving, with the processor via the computing device, a plurality of user input data in response to the one or more computerized cognitive training tasks, wherein the plurality of user input data comprises cohort data corresponding to the one or more instances of the cognitive training regimen; processing, with the processor, the plurality of user input data according to a cognitive assessment model to determine a quantified measure of the one or more cognitive abilities of the user for each instance in the one or more instances of the cognitive training regimen, wherein the cognitive assessment model comprises a hierarchical statistical model; processing, with the processor, the plurality of user input data according to the cognitive assessment model to determine a predicted measure of efficacy for each instance in the one or more instances of the cognitive training regimen, wherein the predicted measure of efficacy comprises a posterior probability distribution in the hierarchical statistical model;

configuring, with the processor, one or more subsequent instances of the cognitive training regimen according to the cognitive assessment model, wherein configuring the one or more subsequent instances comprises configuring or modifying the one or more computerized cognitive training tasks according to the predicted measure of efficacy, wherein the predicted measure of efficacy comprises an expected measure of improvement in the one or more cognitive abilities of the user; and presenting, with the processor via the computing device, the one or more subsequent instances of the cognitive training regimen to the user, wherein the graphical user interface for each subsequent instance in the one or more subsequent instances of the cognitive training regimen is configured to present the one or more computerized cognitive training tasks according to the predicted measure of efficacy.

In accordance with certain aspects of the present disclosure, the method for configuring a user interface within a computerized cognitive training regimen may further comprise estimating, with the processor, an incremental measure of improvement in the one or more cognitive abilities of the user in response to presenting each subsequent instance in the one or more subsequent instances of the cognitive training regimen. In certain embodiments, the method may further comprise determining, with the processor, a target measure of the one or more cognitive abilities of the user according to the cognitive assessment model, wherein the target measure comprises an asymptotic maximum or marginal output value for the incremental measure of improvement in the one or more cognitive abilities of the user. In certain embodiments, the method may further comprise receiving, with the processor via the computing device, a subsequent plurality of user input data in response to the one or more subsequent instances of the cognitive training regimen. In certain embodiments, the method may further comprise processing, with the processor, the subsequent plurality of user input data according to the cognitive assessment model to determine an actual measure of improvement in the one or more cognitive abilities of the user. In certain embodiments, the method may further comprise processing, with the processor, the subsequent plurality of user input data according to the cognitive assessment model to determine an updated predicted measure of efficacy for the one or more computerized cognitive training tasks and/or for the one or more subsequent instances of the cognitive training regimen. In certain embodiments, the method may further comprise configuring, with the processor, the one or more subsequent instances of the cognitive training regimen according to the updated predicted measure of efficacy for each instance in the one or more instances of the cognitive training regimen.

In accordance with further aspects of the method for configuring a user interface within a computerized cognitive training regimen, the predicted measure of efficacy may comprise an argmax for each instance in the one or more instances of the cognitive training regimen according to the cognitive assessment model. In accordance with further aspects of the method for configuring the one or more subsequent instances of the cognitive training regimen according to the updated predicted measure of efficacy. In certain embodiments, the method may further comprise configuring, with the processor, the one or more subsequent instances of the cognitive training regimen according to the argmax for each instance in the one or more instances of the cognitive training regimen.

Further aspects of the present disclosure provide for a system for configuring a user interface within a computerized cognitive training regimen, comprising a processor; and a non-transitory computer readable storage medium communicably engaged with the processor and encoded with processor-executable instructions that, when executed, cause the processor to perform one or more operations comprising presenting one or more instances of the cognitive training regimen, wherein each instance in the one or more instances comprises a graphical user interface configured to present one or more computerized cognitive training tasks comprising one or more computerized stimuli or interactions configured to prompt a targeted response from a user within a specified response window; receiving a plurality of user input data in response to the one or more computerized cognitive training tasks, wherein the plurality of user input data comprises cohort data corresponding to the one or more instances of the cognitive training regimen; processing the plurality of user input data according to a cognitive assessment model to determine a quantified measure of one or more cognitive abilities of the user for each instance in the one or more instances of the cognitive training regimen, wherein the cognitive assessment model comprises a hierarchical statistical model; processing the plurality of user input data according to the cognitive assessment model to determine a predicted measure of efficacy for the cognitive training regimen, wherein the predicted measure of efficacy comprises a posterior probability distribution in the hierarchical statistical model; configuring one or more subsequent instances of the cognitive training regimen according to the cognitive assessment model, wherein configuring the one or more subsequent instances comprises configuring or modifying the one or more computerized cognitive training tasks according to the predicted measure of efficacy, wherein the predicted measure of efficacy comprises an expected measure of improvement in the one or more cognitive abilities of the user; and presenting the one or more subsequent instances of the cognitive training regimen to the user, wherein the graphical user interface for each subsequent instance in the one or more subsequent instances of the cognitive training regimen is configured to present the one or more computerized cognitive training tasks according to the predicted measure of efficacy.

In accordance with certain aspects of the present disclosure, the one or more operations of the processor may further comprise estimating an incremental measure of improvement in the one or more cognitive abilities of the user in response to presenting each subsequent instance in the one or more subsequent instances of the cognitive training regimen. In certain embodiments, the one or more operations of the processor may further comprise determining a target measure of the one or more cognitive abilities of the user according to the cognitive assessment model, wherein the target measure comprises an asymptotic maximum or marginal output value for the incremental measure of improvement in the one or more cognitive abilities of the user. In certain embodiments, the one or more operations of the processor may further comprise receiving a subsequent plurality of user input data in response to the one or more subsequent instances of the cognitive training regimen. In certain embodiments, the one or more operations of the processor may further comprise processing the subsequent plurality of user input data according to the cognitive assessment model to determine an actual measure of improvement in the one or more cognitive abilities of the user. In certain embodiments, the one or more operations of the processor may further comprise processing the subsequent plurality of user input data according to the cognitive assessment model to determine an updated predicted measure of efficacy for the one or more computerized cognitive training tasks. In certain embodiments, the one or more operations of the processor may further comprise configuring the one or more subsequent instances of the cognitive training regimen according to the updated predicted measure of efficacy for each instance in the one or more instances of the cognitive training regimen. In certain embodiments, the one or more operations of the processor may further comprise calculating an argmax for each instance in the one or more instances of the cognitive training regimen according to the cognitive assessment model. In certain embodiments, the one or more operations of the processor may further comprise configuring the one or more subsequent instances of the cognitive training regimen according to the argmax for each instance in the one or more instances of the cognitive training regimen. In certain embodiments, the one or more operations of the processor may further comprise modifying or configuring one or more interface elements of the graphical user interface according to the argmax, wherein the one or more interface elements comprise at least one interface element for the one or more computerized cognitive training tasks.

Still further aspects of the present disclosure provide for a non-transitory computer-readable medium encoded with instructions for commanding one or more processors to execute operations for configuring a user interface within a computerized cognitive training regimen, the operations comprising presenting one or more instances of the cognitive training regimen, wherein each instance in the one or more instances comprises a graphical user interface configured to present one or more computerized cognitive training tasks comprising one or more computerized stimuli or interactions configured to prompt a targeted response from a user within a specified response window; receiving a plurality of user input data in response to the one or more computerized cognitive training tasks, wherein the plurality of user input data comprises cohort data corresponding to the one or more instances of the cognitive training regimen; processing the plurality of user input data according to a cognitive assessment model to determine a quantified measure of one or more cognitive abilities of the user for each instance in the one or more instances of the cognitive training regimen, wherein the cognitive assessment model comprises a hierarchical statistical model; processing the plurality of user input data according to the cognitive assessment model to determine a predicted measure of efficacy for the cognitive training regimen, wherein the predicted measure of efficacy comprises a posterior probability distribution in the hierarchical statistical model; configuring one or more subsequent instances of the cognitive training regimen according to the cognitive assessment model, wherein configuring the one or more subsequent instances comprises configuring or modifying the one or more computerized cognitive training tasks according to the predicted measure of efficacy, wherein the predicted measure of efficacy comprises an expected measure of improvement in the one or more cognitive abilities of the user; and presenting the one or more subsequent instances of the cognitive training regimen to the user, wherein the graphical user interface for each subsequent instance in the one or more subsequent instances of the cognitive training regimen is configured to present the one or more computerized cognitive training tasks according to the predicted measure of efficacy.

The foregoing has outlined rather broadly the more pertinent and important features of the present invention so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be recognized by those skilled in the art that such equivalent structures do not depart from the spirit and scope of the invention.

BRIEF DESCRIPTION OF DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

Figure 1:
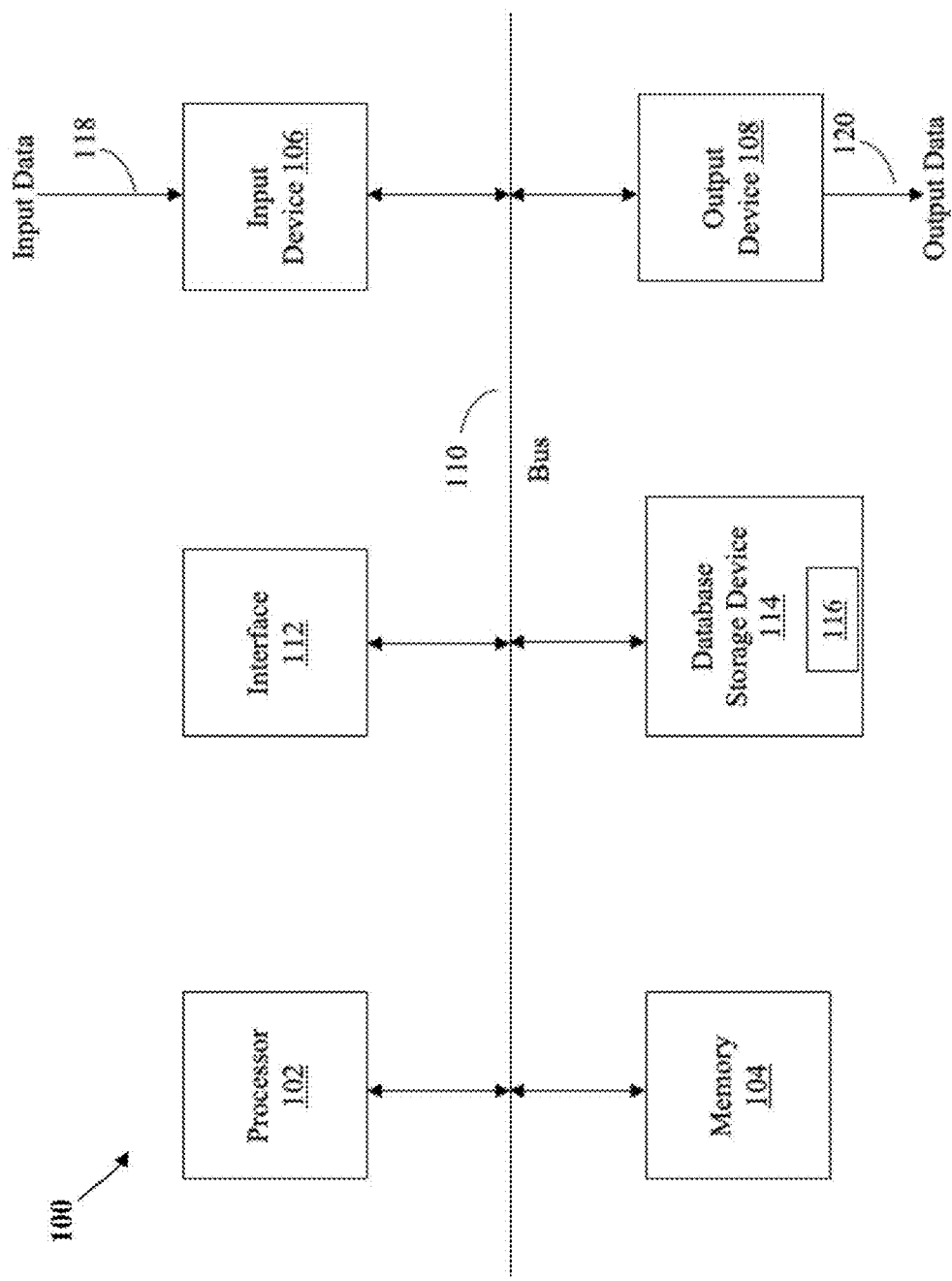
FIG. 1 is a functional block diagram of an exemplary computing system through which certain aspects of the present disclosure may be implemented.

It should be appreciated that all combinations of the concepts discussed in greater detail below (provided such concepts are not mutually inconsistent) are contemplated as being part of the inventive subject matter disclosed herein. It also should be appreciated that terminology explicitly employed herein that also may appear in any disclosure incorporated by reference should be accorded a meaning most consistent with the particular concepts disclosed herein.

Following below are more detailed descriptions of various concepts related to, and embodiments of, inventive methods, devices, systems and computer platform products for analyzing user activity data from one or more sessions of a computerized cognitive training program according to a cognitive assessment model to quantify a relative value to a user in performing computerized cognitive training on each of a set of training tasks and predict a future expected efficacy within a computerized cognitive training program.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes. The present disclosure should in no way be limited to the exemplary implementation and techniques illustrated in the drawings and described below.

Where a range of values is provided, it is understood that each intervening value, to the tenth of the unit of the lower limit unless the context clearly dictates otherwise, between the upper and lower limit of that range and any other stated or intervening value in that stated range is encompassed by the invention. The upper and lower limits of these smaller ranges may independently be included in the smaller ranges, and are also encompassed by the invention, subject to any specifically excluded limit in a stated range. Where a stated range includes one or both of the endpoint limits, ranges excluding either or both of those included endpoints are also included in the scope of the invention.

As used herein, "exemplary" means serving as an example or illustration and does not necessarily denote ideal or best.

As used herein, the term "includes" means includes but is not limited to, the term "including" means including but not limited to. The term "based on" means based at least in part on.

As used herein, the term "stimulus," refers to a sensory event configured to evoke a specified functional response from an individual. The degree and type of response can be quantified based on the individual's interactions with a measuring component (including using sensor devices or other measuring components).

As used in certain examples herein, the term "user activity data" refers to data collected from measures of an interaction of a user with a software program, product and/or platform.

As used herein, the term "computerized stimuli or interaction" or "CSI" refers to a computerized element that is presented to a user to facilitate the user's interaction with a stimulus or other interaction. As non-limiting examples, the computing device can be configured to present auditory stimulus (presented, e.g., as an auditory computerized adjustable element or an element of a computerized auditory task) or initiate other auditory-based interaction with the user, and/or to present vibrational stimuli (presented, e.g., as a vibrational computerized adjustable element or an element of a computerized vibrational task) or initiate other vibrational-based interaction with the user, and/or to present tactile stimuli (presented, e.g., as a tactile computerized adjustable element or an element of a computerized tactile task) or initiate other tactile-based interaction with the user, and/or to present visual stimuli or initiate other visual-based interaction with the user.

In an example where the computing device is configured to present visual CSI, the CSI can be rendered as at least one user interface to be presented to a user. In some examples, the at least one user interface is configured for measuring responses as the user interacts with a CSI computerized element rendered at the at least one user interface. In a non-limiting example, the user interface can be configured such that the CSI computerized element(s) are active, and may require at least one response from a user, such that the user interface is configured to measure data indicative of the type or degree of interaction of the user with the platform product. In another example, the user interface can be configured such that the CSI computerized element(s) are a passive and are presented to the user using the at least one user interface but may not require a response from the user. In this example, the at least one user interface can be configured to exclude the recorded response of an interaction of the user, to apply a weighting factor to the data indicative of the response (e.g., to weight the response to lower or higher values), or to measure data indicative of the response of the user with the platform product as a measure of a misdirected response of the user (e.g., to issue a notification or other feedback to the user of the misdirected response).

As used in certain examples herein, the term "user" means an individual participating in a computerized cognitive training regimen and/or an individual interacting with an instance of a computerized cognitive assessment or computerized cognitive training program.

As used herein the terms "digital health intervention (DHI)" and "software as a medical device (SaMD)" may be used interchangeably and encompass any software program, product, or platform, including any software/hardware combination, being designed and/or utilized for any general or targeted medical or personal wellness purpose, including but not limited to the treatment, diagnosis, management, prevention, cure, or generation or provision of clinical, health, and/or wellness insights or recommendations to one or more users for one or more medial, health or personal wellness purpose; including any software program, product, or platform, including any software/hardware combination, being designed and/or utilized to promote healthy behaviors, improve outcomes in people with long term conditions such as cardiovascular disease, diabetes and mental health conditions and provide remote access to effective treatments; for example, computerized cognitive behavioral therapy for mental health and somatic problems; and may further encompass one or more software program, product or platform, including any product(s), program(s) and/or platform(s) that incorporate any combination of hardware and software, that is/are directly therapeutically active in treating and/or targeting one or more neurological circuits related to one or more neurological, psychological and/or somatic conditions, diseases, and/or disorders, rather than just being a component of overall treatment.

The term "task" refers to a goal and/or objective to be accomplished by an individual who provides a response to a particular stimulus. For example, the individual would have been instructed to perform a specific goal. The "task" can serve as the baseline cognitive function that is being performed and measured, and to which interference is added. Thus, a "task" often refers to the main goal that an individual is instructed to perform in either the presence or absence of interference.

All definitions, as defined and used herein, should be understood to control over dictionary definitions, definitions in documents incorporated by reference, and/or ordinary meanings of the defined terms. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

An exemplary system, method, and computer platform product according to the principles herein provides for an adaptive cognitive training platform configured to quantify the relative value to a user of performing additional cognitive training on each of a set of training tasks on-the-fly by predicting the future expected efficacy of such tasks according to one or more cognitive assessment model. In accordance with various aspects of the present disclosure, an adaptive cognitive training platform is configured to process user activity data from one or more instances of a computerized cognitive training program according to the cognitive assessment model to determine a baseline cognitive assessment for one or more cognitive abilities of a user. The cognitive assessment model may be configured to further process the user activity data to predict a relative value or measure of efficacy for one or more computerized stimuli or interactions within the computerized cognitive training program. In accordance with various aspects of the present disclosure, an adaptive cognitive training platform is configured to configure, modify and/or present one or more interface elements of a graphical user interface for one or more subsequent instances of the computerized cognitive training program according to the predicted relative value or measure of efficacy for the one or more computerized stimuli or interactions.

An exemplary system, method, and computer platform product according to the principles herein provides for an adaptive cognitive training platform configured to process user activity data from one or more instances of a computerized cognitive training program according to the cognitive assessment model to determine and/or predict one or more of (1) a baseline cognitive assessment for one or more cognitive abilities of a user, (2) a relative value or measure of efficacy for one or more computerized stimuli or interactions within the computerized cognitive training program, and (3) a personalized cognitive training regimen for the computerized cognitive training program.

Certain aspects of the present disclosure provide for a method, system and computer platform product for analyzing user activity data according within a computerized cognitive training program according to a cognitive assessment model. According to various aspects of the present disclosure, the cognitive assessment model may be configured to predict a measure of efficacy in improving one or more cognitive abilities of a user across one or more instances of the computerized cognitive training program. According to various aspects of the present disclosure, the cognitive assessment model may be configured to predict the relative value of presenting one or more tasks to the user across one or more instances of the computerized cognitive training program. In certain embodiments, the cognitive assessment model may comprise a hierarchical statistical model comprising a Bayesian hierarchical model.

Turning now descriptively to the drawings, in which similar reference characters denote similar elements throughout the several views, FIG. 1 depicts a computing system in which certain illustrated embodiments of the present invention may be implemented.

Referring now to FIG. 1, a processor-implemented computing device in which one or more aspects of the present disclosure may be implemented is shown. According to an embodiment, a processing system 100 may generally comprise at least one processor 102, a memory 104, an input device 106 for receiving input data 118 and an output device 108 that produces output data 120 coupled together with at least one bus 110. In certain embodiments, input device 106 and output device 108 could be the same device. An interface 112 can also be provided for coupling the processing system 100 to one or more peripheral devices, for example interface 112 could be a PCI card or PC card. At least one database storage device 114 which houses at least one database 116 can also be provided. The memory 104 can be any form of memory device, for example, volatile or non-volatile memory, solid state storage devices, magnetic devices, and the like. The processor 102 could comprise more than one distinct processing device, for example to handle different functions within the processing system 100. Input device 106 receives input data 118 and can comprise, for example, a keyboard, a pointer device such as a pen-like device or a mouse, audio receiving device for voice-controlled activation such as a microphone, data receiver or antenna such as a modem or wireless data adaptor, data acquisition card, and the like. Input data 118 could come from different sources, for example keyboard instructions in conjunction with data received via a network. Output device 108 produces or generates output data 120 and can comprise, for example, a display device or monitor in which case output data 120 is visual, a printer in which case output data 120 is printed, a port for example a USB port, a peripheral component adaptor, a data transmitter or antenna such as a modem or wireless network adaptor, and the like. Output data 120 could be distinct and derived from different output devices, for example a visual display on a monitor in conjunction with data transmitted to a network. A user could view data output, or an interpretation of the data output, on, for example, a monitor or using a printer. The storage device 114 can be any form of data or information storage means, for example, volatile or non-volatile memory, solid state storage devices, magnetic devices, and the like.

In use, the processing system 100 is adapted to allow data or information to be stored in and/or retrieved from, via wired or wireless communication means, at least one database 116. The interface 112 may allow wired and/or wireless communication between the processing unit 102 and peripheral components that may serve a specialized purpose. In general, the processor 102 can receive instructions as input data 118 via input device 106 and can display processed results or other output to a user by utilizing output device 108. More than one input device 106 and/or output device 108 can be provided. It should be appreciated that the processing system 100 may be any form of terminal, server, specialized hardware, or the like.

It is to be appreciated that the processing system 100 may be a part of a networked communications system. Processing system 100 could connect to a network, for example the Internet or a WAN. Input data 118 and output data 120 could be communicated to other devices via the network. The transfer of information and/or data over the network can be achieved using wired communications means or wireless communications means. A server can facilitate the transfer of data between the network and one or more databases. A server and one or more databases provide an example of an information source.

Thus, the processing computing system environment 100 illustrated in FIG. 1 may operate in a networked environment using logical connections to one or more remote computers. The remote computer may be a personal computer, a server, a router, a network PC, a peer device, or other common network node, and typically includes many or all of the elements described above.

It is to be further appreciated that the logical connections depicted in FIG. 1 include a local area network (LAN) and a wide area network (WAN) but may also include other networks such as a personal area network (PAN). Such networking environments are commonplace in offices, enterprise-wide computer networks, intranets, and the Internet. For instance, when used in a LAN networking environment, the computing system environment 100 is connected to the LAN through a network interface or adapter. When used in a WAN networking environment, the computing system environment typically includes a modem or other means for establishing communications over the WAN, such as the Internet. The modem, which may be internal or external, may be connected to a system bus via a user input interface, or via another appropriate mechanism. In a networked environment, program modules depicted relative to the computing system environment 100, or portions thereof, may be stored in a remote memory storage device. It is to be appreciated that the illustrated network connections of FIG. 1 are exemplary and other means of establishing a communications link between multiple computers may be used.

FIG. 1 is intended to provide a brief, general description of an illustrative and/or suitable exemplary environment in which various embodiments of the invention may be implemented. FIG. 1 is an example of a suitable environment and is not intended to suggest any limitation as to the structure, scope of use, or functionality of an embodiment of the present invention. A particular environment should not be interpreted as having any dependency or requirement relating to any one or combination of components illustrated in an exemplary operating environment. For example, in certain instances, one or more elements of an environment may be deemed not necessary and omitted. In other instances, one or more other elements may be deemed necessary and added.

In the description that follows, certain embodiments may be described with reference to acts and symbolic representations of operations that are performed by one or more computing devices, such as the computing system 100 of FIG. 1. As such, it will be understood that such acts and operations, which are at times referred to as being computer-executed, include the manipulation by the processor of the computer of electrical signals representing data in a structured form. This manipulation transforms the data or maintains them at locations in the memory system of the computer, which reconfigures or otherwise alters the operation of the computer in a manner understood by those skilled in the art. The data structures in which data is maintained are physical locations of the memory that have particular properties defined by the format of the data. However, while an embodiment is being described in the foregoing context, it is not meant to be limiting as those of skill in the art will appreciate that the acts and operations described hereinafter may also be implemented in hardware.

Embodiments of the present invention can be implemented with numerous other general-purpose or special-purpose computing devices, systems or configurations. Examples of well-known computing systems, environments, and configurations suitable for use in embodiment of the invention include, personal computers, handheld or laptop devices, personal digital assistants, multiprocessor systems, microprocessor-based systems, set top boxes, programmable consumer electronics, network, minicomputers, server computers, game server computers, web server computers, mainframe computers, and distributed computing environments that include any of the above systems or devices.

Various embodiments of the invention will be described herein in a general context of computer-executable instructions, such as program modules, being executed by a computer. Generally, program modules include routines, programs, objects, components, data structures, and the like, that perform particular tasks or implement particular abstract data types. In certain embodiments, distributed computing environments where tasks are performed by remote processing devices that are linked through a communications network may also be employed. In distributed computing environments, program modules may be located in both local and remote computer storage media including memory storage devices.

With the general computing system environment 100 of FIG. 1 being shown and discussed above, the following description and remaining figures pertain to various exemplary embodiments of the present invention generally relating to methods and systems adaptive configuration of user interfaces and program instances within a computerized cognitive training regimen. In general, the methods described herein involve presenting, with a processor communicably engaged with a computing device, one or more instances of the cognitive training regimen to a user, the cognitive training regimen comprising one or more computerized cognitive training tasks presented via a graphical user interface, wherein the one or more computerized cognitive training tasks are configured to target one or more cognitive abilities of the user; receiving, with the processor via the computing device, a plurality of user input data in response to the one or more computerized cognitive training tasks, wherein the plurality of user input data comprises cohort data corresponding to the one or more instances of the cognitive training regimen; processing, with the processor, the plurality of user input data according to a cognitive assessment model to determine a quantified measure of the one or more cognitive abilities of the user for each instance in the one or more instances of the cognitive training regimen, wherein the cognitive assessment model comprises a hierarchical statistical model; processing, with the processor, the plurality of user input data according to the cognitive assessment model to determine a predicted measure of efficacy for each instance in the one or more instances of the cognitive training regimen, wherein the predicted measure of efficacy comprises a posterior probability distribution in the hierarchical statistical model; configuring, with the processor, one or more subsequent instances of the cognitive training regimen according to the cognitive assessment model, wherein configuring the one or more subsequent instances comprises configuring or modifying the one or more computerized cognitive training tasks according to the predicted measure of efficacy, wherein the predicted measure of efficacy comprises a predicted incremental measure of improvement in the one or more cognitive abilities of the user for each subsequent instance in the one or more subsequent instances of the cognitive training regimen; and presenting, with the processor via the computing device, the one or more subsequent instances of the cognitive training regimen to the user, wherein the graphical user interface for each subsequent instance in the one or more subsequent instances of the cognitive training regimen is configured to present the one or more computerized cognitive training tasks according to the predicted measure of efficacy.

Figure 2:
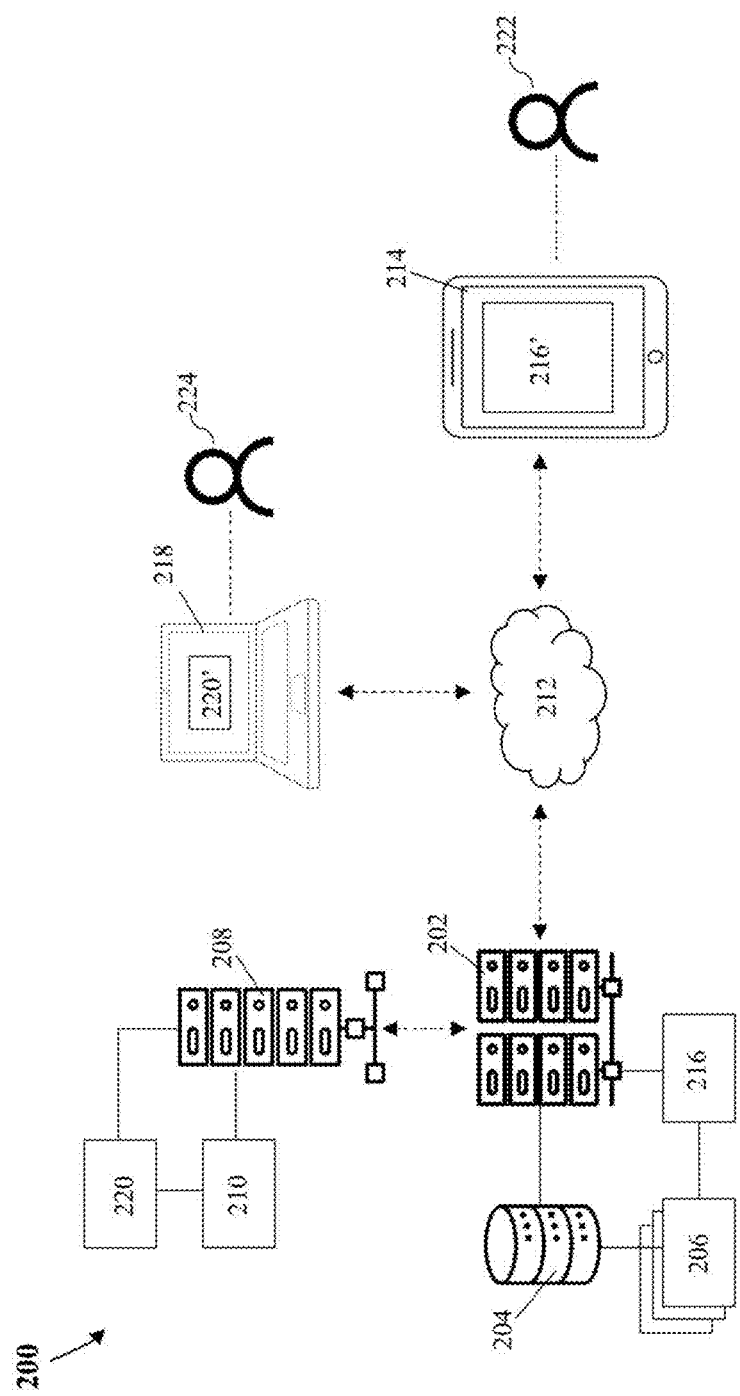
FIG. 2 is an architecture diagram of an adaptive cognitive assessment and training system, in accordance with certain aspects of the present disclosure.

Referring now to FIG. 2, an architecture diagram of an adaptive cognitive assessment and training system 200 is shown. In accordance with certain aspects of the present disclosure, adaptive cognitive assessment and training system 200 is generally comprised of a cognitive training application server 202, an application database 204 and a cognitive assessment server 208. In certain embodiments, adaptive cognitive assessment and training system 200 comprises one or more cognitive training engine 206 and a cognitive training application 216 executing on cognitive training application server 202. In accordance with various aspects of the present disclosure, cognitive training application 216 comprises a digital health intervention (DHI) and/or a software as a medical device (SaMD) program product configured to deliver a plurality of therapeutically active cognitive training tasks via one or more graphical user interfaces to an end user. Adaptive cognitive assessment and training system 200 may further comprise a cognitive assessment model engine 210 and a cognitive assessment application 220 executing on cognitive assessment server 208. Adaptive cognitive assessment and training system 200 may further comprise a user device 214 configured to execute a client-side instance of cognitive assessment application 216' to a user 222. In accordance with certain aspects of the present disclosure, user 222 is an individual participating in a computerized cognitive treatment regimen, for which client-side instance of cognitive training application 216' may comprise an instance of a cognitive assessment session or a cognitive training session. User device 214 may comprise a computing device such as a tablet computer, smart phone, personal computer, laptop computer and the like. User device 214 may be communicably engaged with cognitive training application server 202 via a communications network interface 212. In certain embodiments, adaptive cognitive assessment and training system 200 may further comprise an administrator device 218 configured to execute a client-side instance of cognitive assessment application 220' for an administrator user 224. In accordance with certain embodiments, user device 218 may comprise a computing device such as a tablet computer, smart phone, personal computer, laptop computer and the like. User device 218 may be communicably engaged with cognitive training application server 202 via communications network interface 212.

In some embodiments, cognitive training engine 206 may be communicably engaged with application database 204 to communicate data thereto and receive data therefrom. Cognitive training engine 206 may comprise a plurality of instructions for execution by a processor of cognitive training application server 202 to command one or more data processing operations for one or more computerized stimuli or interactions or tasks within a computerized cognitive training application 216. In certain embodiments, cognitive training engine 206 may comprise one or more data processing algorithms and/or other encapsulated software functionality configured to control one or more functions, graphical elements or parameters of one or more cognitive training tasks according to one or more clinically validated stimulus-response patterns. For example, cognitive training engine 206 may comprise one or more algorithm configured to render one or more graphical user interface elements and process user-generated inputs for one or more CSIs and/or tasks according to one or more clinically validated stimulus-response patterns designed to target neural systems involved in attentional control, including focus, interference processing and multitasking (fronto-parietal areas of the brain); attention, impulsivity, working memory, and goal management (fronto-parieto-cerebellar areas of the brain); spatial navigation, memory, and planning and organization (extended hippocampal system in the brain). In accordance with various embodiments, cognitive training engine 206 may comprise an encapsulated block of functionality configured to drive one or more user-prompts, response-deadlines procedures, task difficulty level and/or graphical elements of one or more CSIs or tasks within computerized cognitive training application 216. In accordance with various aspects of the present disclosure, computerized cognitive training application 216 may comprise two or more distinct cognitive training engines 206 associated with different clinically validated stimulus-response patterns designed to target different target neural systems. In accordance with said embodiments, computerized cognitive training application 216 may comprise a multi-engine cognitive training program configured to render/present two or more types of CSIs or tasks designed to target different neural systems of user 222. In accordance with said embodiments, computerized cognitive training application 216 may be configured to render/present two or more types of CSIs via client-side instance of cognitive training application 216' and receive, in response thereto, a plurality of user-generated inputs from user 222 via user device 218. Cognitive training application 216' may comprise one or more protocols for communicating the plurality of user-generated input data to cognitive training application server 202. Cognitive training application server 202 may be configured to store the plurality of user-generated input data in application database 204 for each session instance of cognitive training application 216'.

In accordance with certain aspects of the present disclosure, adaptive cognitive assessment and training system 200 may further comprise an adaptive cognitive assessment engine 210 executing on cognitive assessment server 208. Adaptive cognitive assessment engine 210 may comprise one or more instructions for commanding a processor of cognitive assessment server 208 to perform one or more operations of a cognitive assessment model. The cognitive assessment model may be configured to process the user-generated input data to determine a quantified measure of cognitive skills for user 222 based on performance on one or more cognitive training tasks presented within session instance of cognitive training application 216'. In certain embodiments, the cognitive assessment model may be configured as a hierarchical statistical model; for example, a Bayesian hierarchical model comprising multiple levels (hierarchical form) that estimates the parameters of the posterior distribution using the Bayesian method. In certain embodiments, the one or more operations may comprise operations for processing a plurality of user input data to determine a quantified measure of one or more cognitive abilities of user 222. In certain embodiments, the one or more operations may comprise operations for processing the plurality of user input data according to the cognitive assessment model to determine a predicted measure of efficacy for the computerized cognitive training regimen, wherein the predicted measure of efficacy comprises a posterior probability distribution in the hierarchical statistical model; for example, as described in more detail in FIGS. 3A-3F below.

Referring now to FIGS. 3A-3F, various graphical diagrams of data processing outputs of a cognitive assessment model within an adaptive cognitive assessment and training system are shown. In accordance with various aspects of the present disclosure, an adaptive cognitive assessment and training system may be configured as adaptive cognitive assessment and training system 200 and a cognitive assessment model may be configured as one or more data processing algorithms of adaptive cognitive assessment engine 210 and/or cognitive training engine 206 (as shown and described in FIG. 2). In accordance with various embodiments, the adaptive cognitive assessment and training system may be configured to calculate/quantify a cognitive ability level (i.e., performance metric) of a user (e.g., user 222 of FIG. 2) across one or more cognitive assessments and/or training instances of a computerized cognitive training regimen. Cognitive assessment measurements may be interleaved with training sessions, as shown in graph 302 and graph 304. Cognitive assessment measurements may comprise observed data to be applied to the cognitive assessment model, wherein the cognitive assessment model is configured to predict future cognitive assessment measurements for one or more future instances of the computerized cognitive training regimen.

Figure 3B:
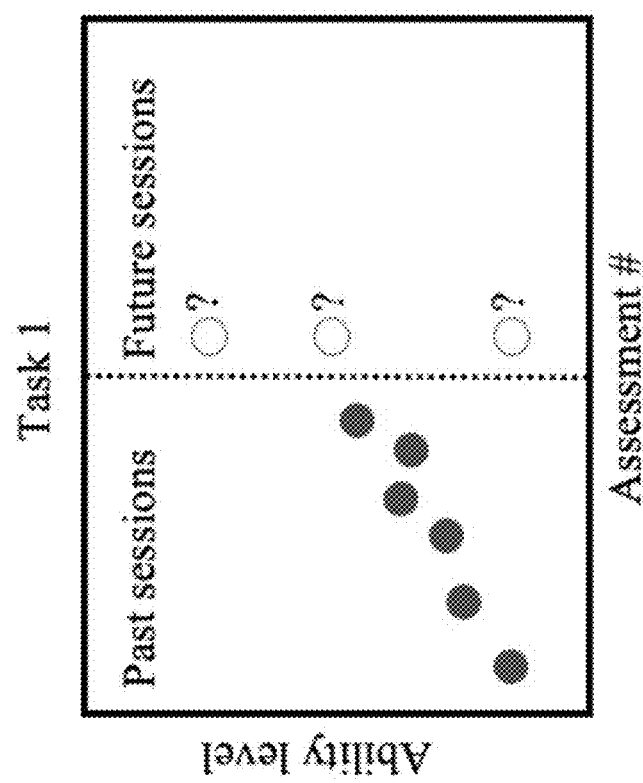
FIGS. 3A-3F are graphical diagrams of user assessment data and statistical analyses within an adaptive cognitive assessment and training system, in accordance with certain aspects of the present disclosure.
Figure 3A:
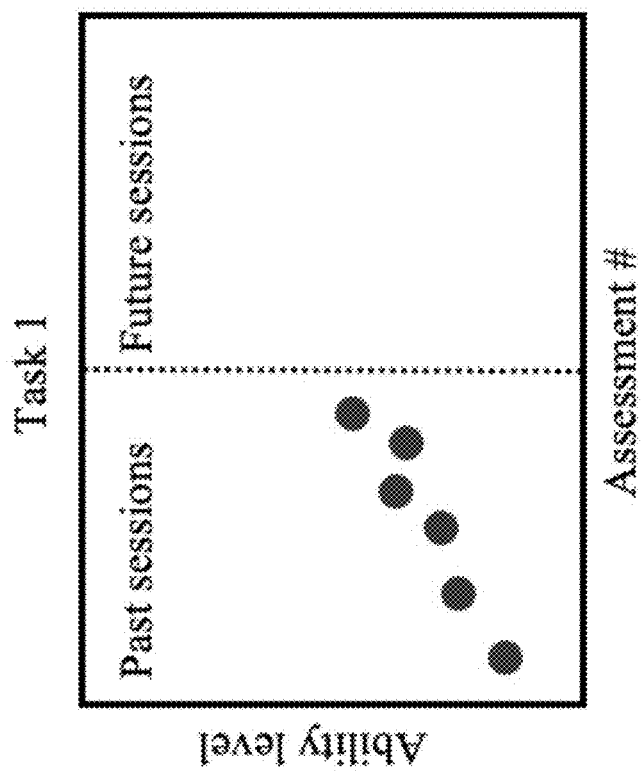
Figure 3D:
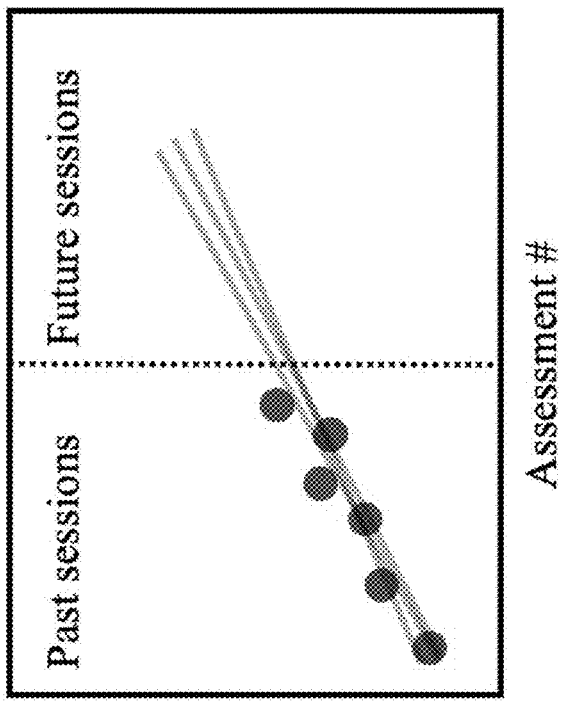
Figure 3C:
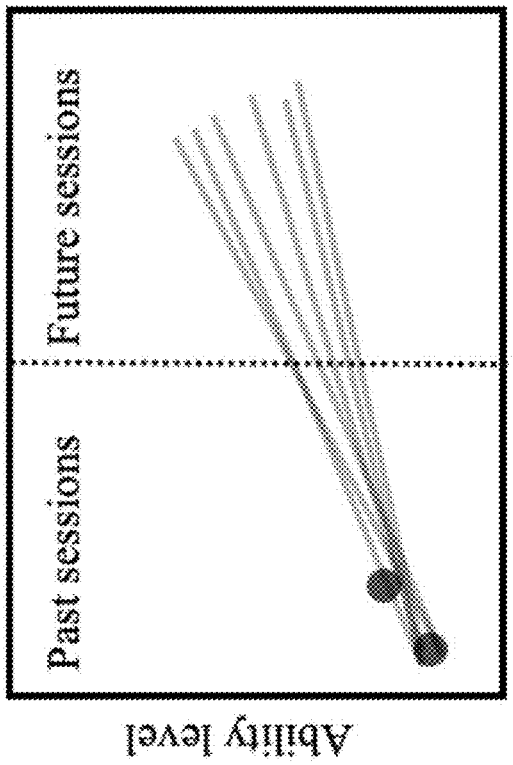

As shown in FIGS. 3C-3D, the cognitive assessment model may comprise a hierarchical statistical model, such as a Bayesian hierarchical model, comprising multiple sub-models (i.e., hierarchical levels) to estimate parameters of a posterior distribution of user performance data across one or more prior sessions of the computerized cognitive training regimen. The sub-models may be combined to form the hierarchical model of the cognitive assessment model. In accordance with certain embodiments, the cognitive assessment model may be configured to integrate the observed user performance data (i.e., user performance data across one or more prior sessions of the computerized cognitive training regimen) and account for all the uncertainty that is present in the posterior distribution of said observed user performance data. In instances with limited or uninformative prior observed data, the posterior distribution of the cognitive assessment model may yield a narrower posterior distribution to reflect a higher degree of uncertainty in the cognitive assessment model; for example, as shown in FIG. 3C. In instances with more informative prior observed data and/or as additional prior observed data becomes available, the posterior distribution of the cognitive assessment model may yield a narrower posterior distribution to reflect a lower degree of uncertainty in the cognitive assessment model; for example, as shown in FIG. 3D.

Figure 3E:
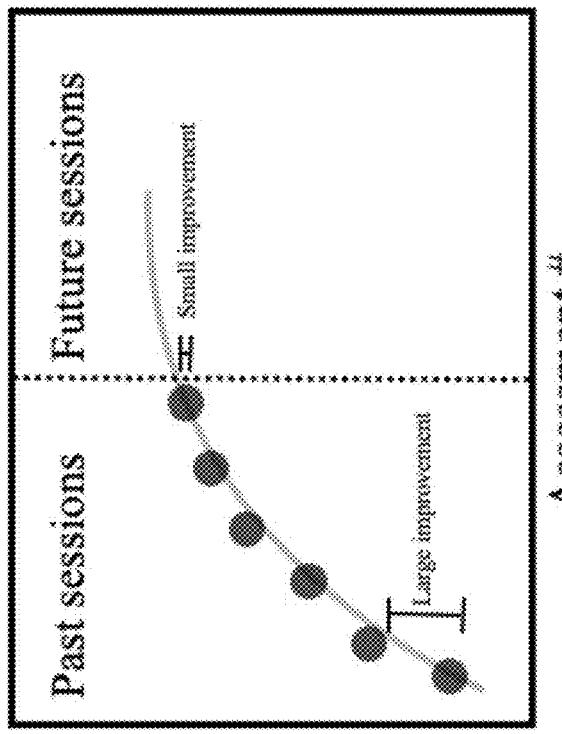
Figure 3F:
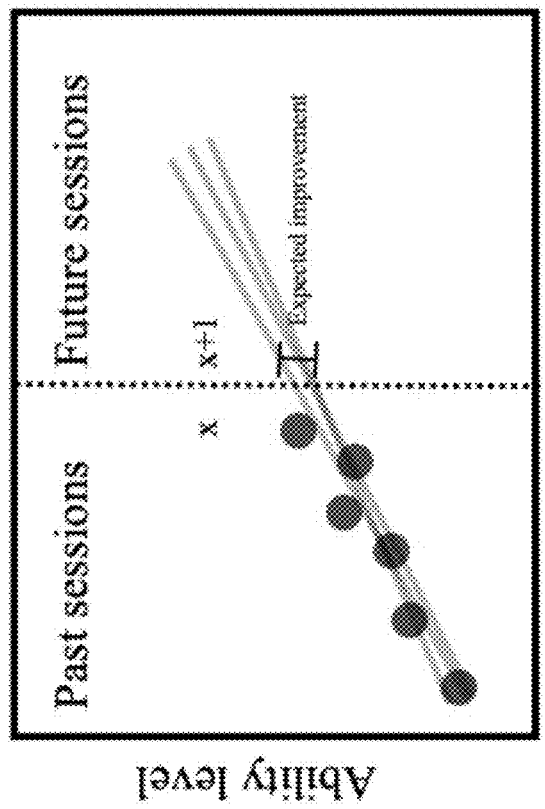

As shown in FIGS. 3E-3F, the cognitive assessment model may be configured to predict an expected measure of improvement in the cognitive ability level of a user (i.e., predicted efficacy) across successive sessions of the computerized cognitive training regimen according to the calculated posterior distribution. For example, as shown in FIG. 3E, the cognitive assessment model may be configured to express the posterior distribution as a linear function, where the predicted efficacy comprises an expected improvement from x to x+1 between each successive future session of the computerized cognitive training regimen. In certain embodiments, as shown in FIG. 3F, the cognitive assessment model may be configured to express the posterior distribution as a non-linear function, where the predicted efficacy comprises a non-linear (i.e., diminishing) degree of improvement for each successive future session of the computerized cognitive training regimen.

Figure 4A:
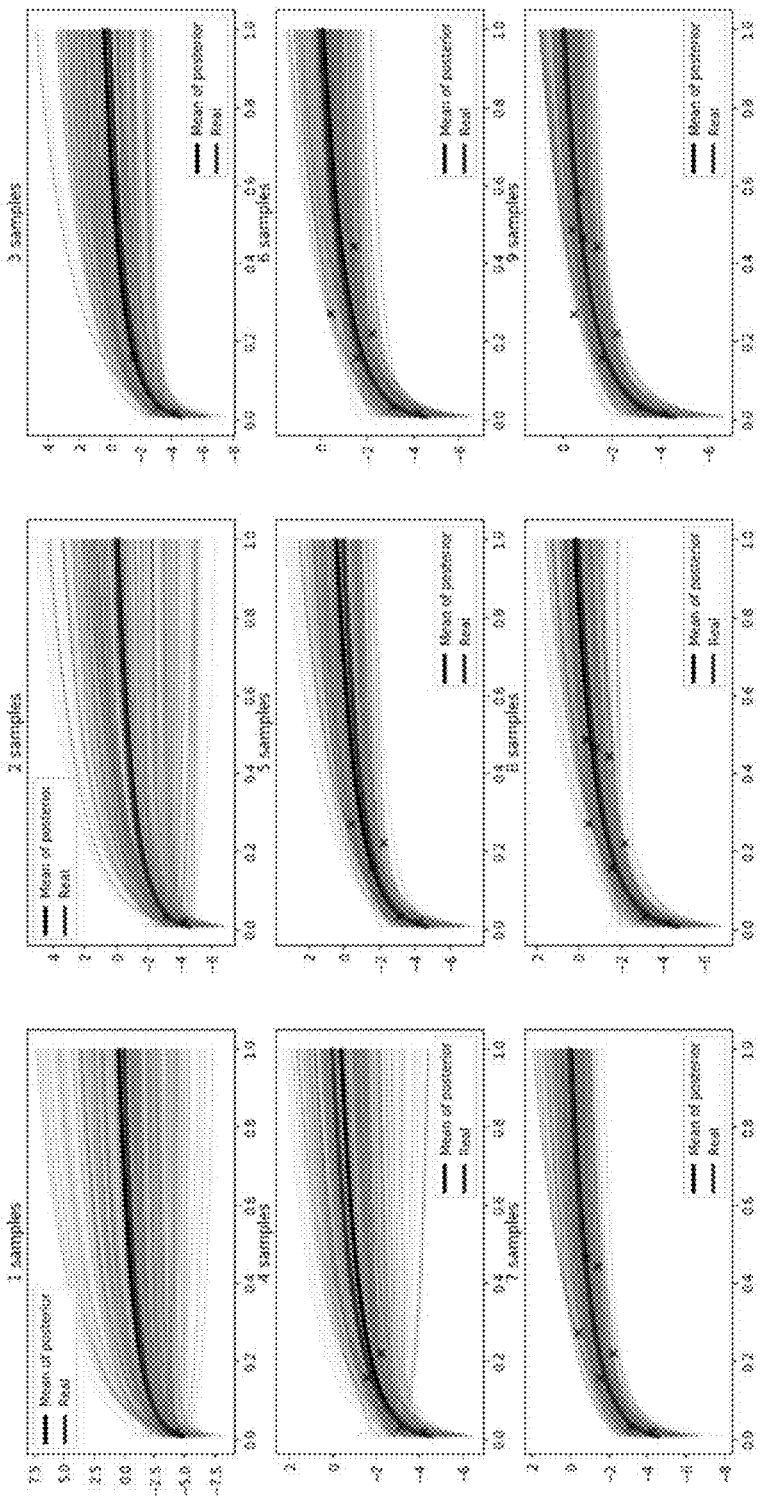
FIG. 4A-4D are graphical diagrams of user assessment data and statistical analyses within an adaptive cognitive assessment and training system, in accordance with certain aspects of the present disclosure.

Referring now to FIGS. 4A-4D, various graphical illustrations of simulated posterior distributions of the cognitive assessment model are shown. In accordance with certain aspects of the present disclosure, the cognitive assessment model may be configured to continuously calculate an updated probability estimate as additional evidence on the prior distribution is acquired (e.g., as additional sessions of the computerized cognitive training regimen are completed by the user). FIG. 4A illustrates the posterior distribution across nine simulated sessions of the computerized cognitive training regimen, in which the simulated sessions comprise a cohort within the cognitive assessment model. FIG. 4A illustrates the progressive integration of the observed user performance data (i.e., observed cognitive ability level) between the sub-models in the hierarchical model to progressively predict the degree of uncertainty in the posterior distribution (i.e., probability estimate). When the prior observed data is limited or otherwise uninformative, the cognitive assessment model may be configured to apply a higher degree of uncertainty to the posterior distribution; for example, as shown in the "1 samples" plot in FIG. 4A, the cognitive assessment model yields a broad posterior distribution (i.e., the sub-models in the hierarchical model are less integrated) to account for a higher degree of uncertainty or lower probability estimate in the model due to the limited/uninformative observed priors. As additional user performance data is collected in successive sessions of the computerized cognitive training regimen, the cognitive assessment model incorporates the observed data as additional evidence on the prior distribution and updates the probability estimate as uncertainty in reduced. For example, as shown in the "9 samples" plot in FIG. 4A, the cognitive assessment model yields a narrower posterior distribution (i.e., the sub-models in the hierarchical model are more integrated) to account for greater certainty in the model in light of the additional observed data in the model cohort.

Figure 4B:
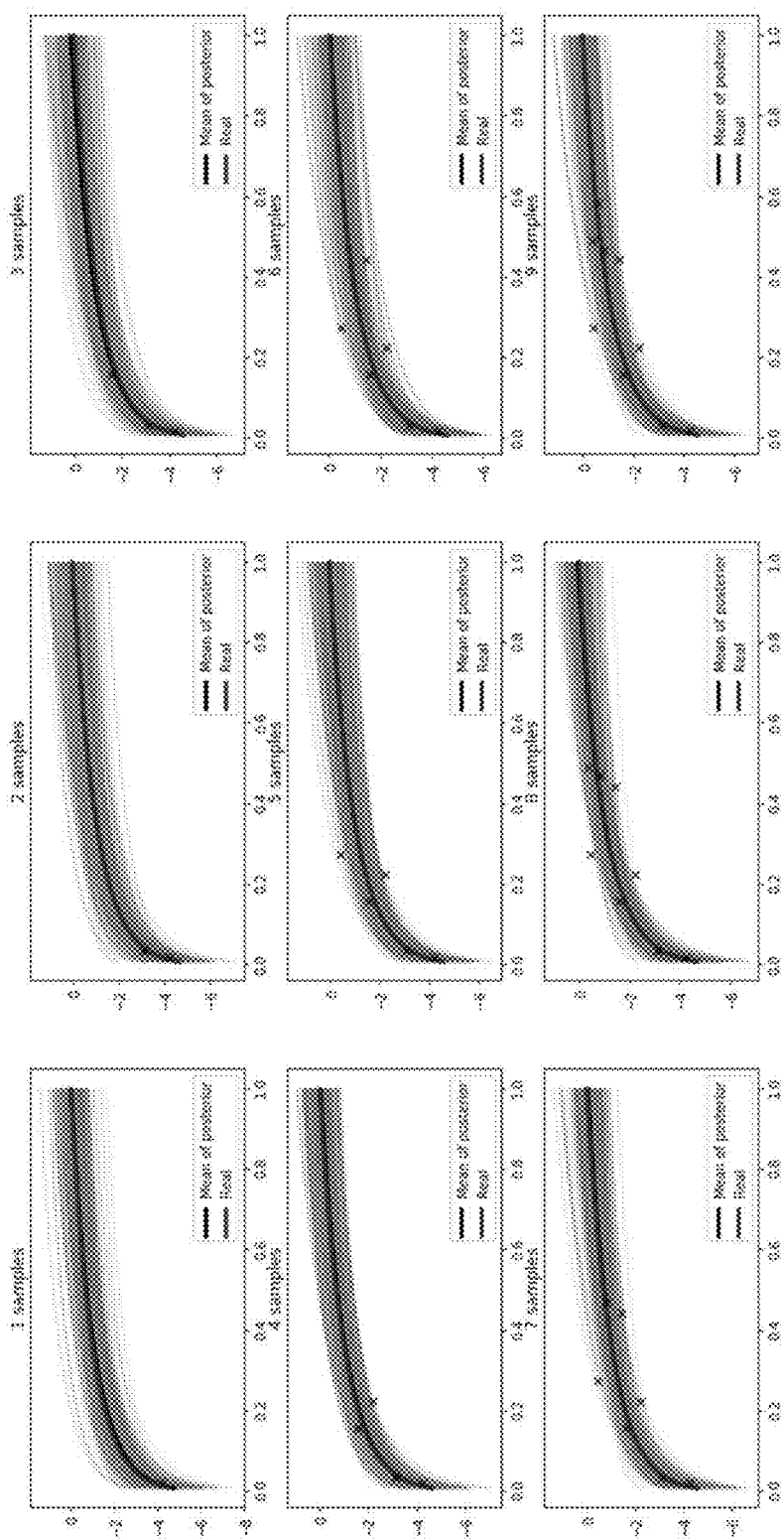

As shown in FIG. 4B, the cognitive assessment model may comprise one or more parameters configured to assess a degree of informativeness in the prior observed data. For example, the one or more parameters may include certain a priori information about the user and/or prior model performance information. When the parameters of the cognitive assessment model suggest a strong degree of informativeness in the prior observed data, the cognitive assessment model may be configured to reduce the degree of uncertainty present in the posterior distribution, even where the number of observed priors is otherwise limited. FIG. 4B illustrates the posterior distribution across nine simulated sessions of the computerized cognitive training regimen, in which the prior observed user performance data for one or more of the simulated sessions comprises a strong degree of informativeness. In accordance with certain aspects of the present disclosure, the parameters of the cognitive assessment model may comprise one or more hyperparameters or hyperpriors configured to assess the degree of informativeness of the prior observed data. For example, one or more hyperparameters may include one or more variables within the prior observed data (e.g., user performance metrics, observed stimulus-response patterns for the user, and the like) and one or more hyperpriors may include one or more variables within the prior distribution (e.g., relationship between variables across priors, degree of model fit across priors, changes in model assumptions, and the like).

Figure 4C:
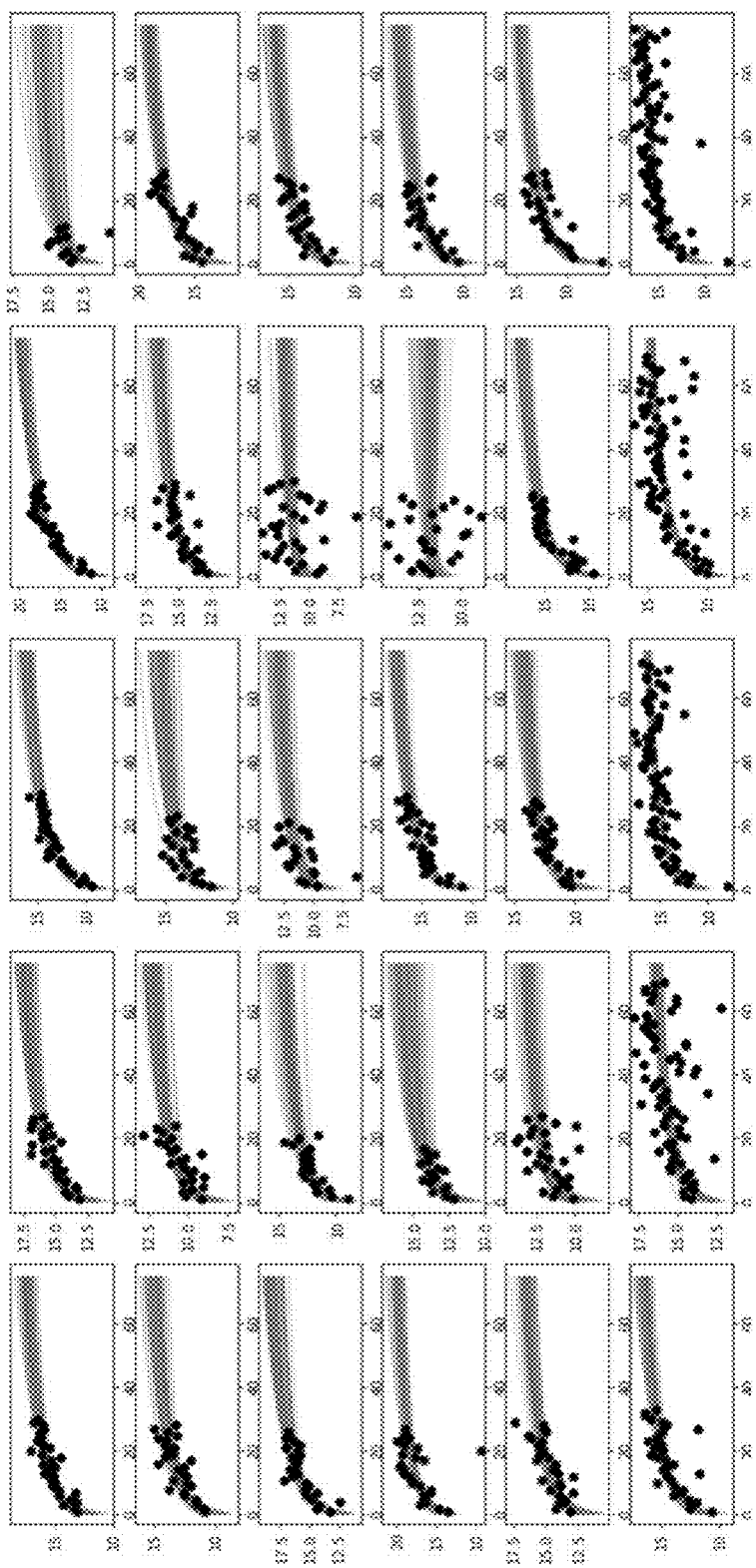
Figure 4D:
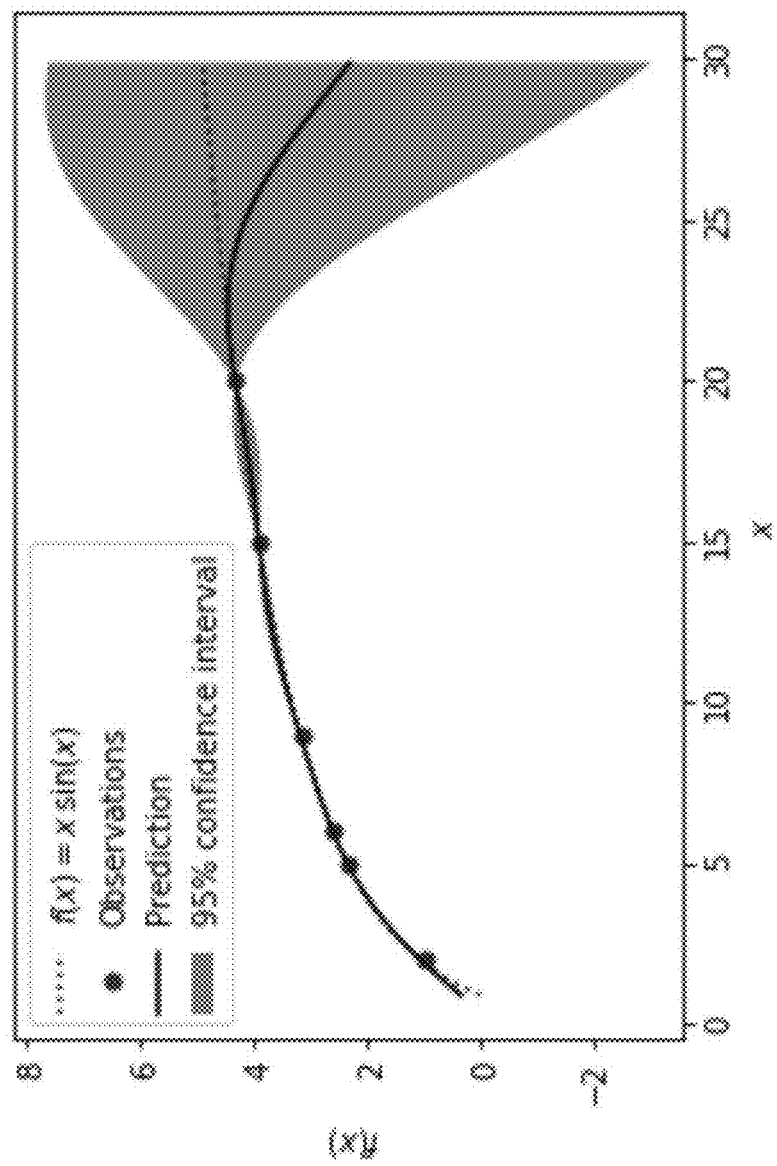

In accordance with certain aspects of the present disclosure, the adaptive cognitive assessment and training system may be configured to continuously monitor user performance data across one or more instances of the computerized cognitive training program and/or across one or more computerized cognitive assessments. In certain embodiments, the adaptive cognitive assessment and training system may continuously monitor user performance data across one or more individual users, one or more user cohorts, one or more user groups (as defined by one or more relationships between user data and model variable), and/or all users in an application database (e.g., application database 204 of FIG. 2). As shown in FIG. 4C, the adaptive cognitive assessment and training system may be configured to (i) continuously collect/receive cognitive assessment/performance data for one or more users across subsequent instances of the computerized cognitive assessment/training program, (ii) process the cognitive assessment/performance data via the cognitive assessment model to continuously update the posterior distribution and/or one or more model parameters and (iii) continuously compute efficacy predictions for each user engaged in the computerized cognitive training regimen. In accordance with certain embodiments, the cognitive assessment model may comprise one or more different constituent algorithms and/or data models configured to compute an efficacy prediction for the computerized cognitive training regimen and/or each successive training instance of the computerized cognitive training application and/or one or more CSIs/tasks presented within the computerized cognitive training application. In some embodiments, the cognitive assessment model may comprise a hierarchical framework in which different constituent algorithms/models are utilized based on different model parameters and/or conditions. For example, as shown in FIG. 4D, the cognitive assessment model may comprise a Gaussian Process Regression framework to compute an efficacy prediction when no prior data or model is available. In accordance with certain embodiments, the cognitive assessment model may comprise one or more machine learning ensemble comprising two or more constituent learning algorithms and/or data models. The adaptive cognitive assessment and training system may further comprise a machine learning framework configured analyze a different dataset and/or different variables/parameters than that of the cognitive assessment model for the purposes of assessing model performance, configuring model parameters, and/or performing one or more secondary/longitudinal analysis within the adaptive cognitive assessment and training system (e.g., safety, performance, efficacy, user outcomes and the like).

Figure 5B:
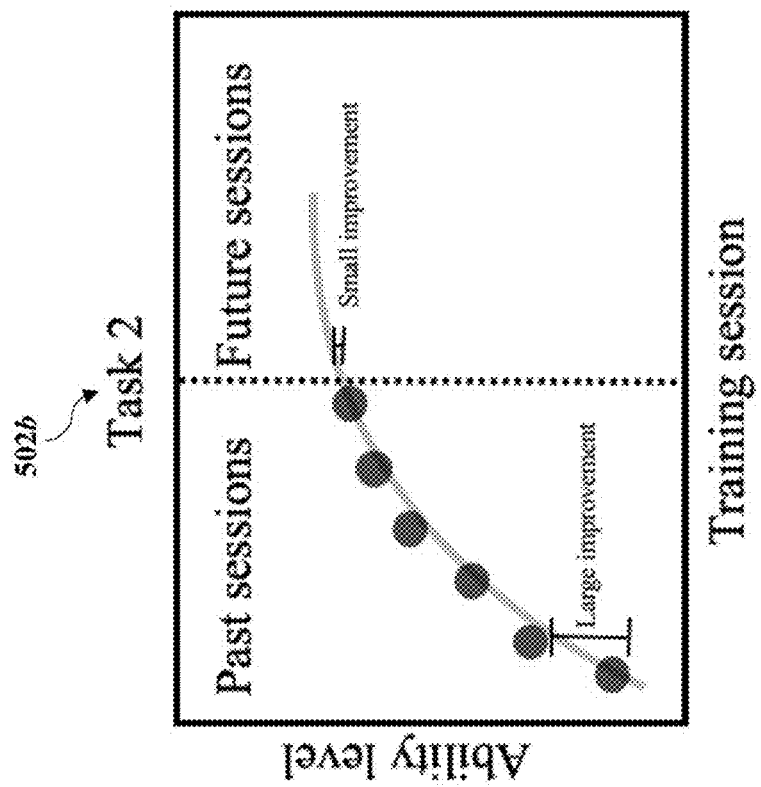
FIG. 5A-5D are graphical diagrams of user assessment data and statistical analyses within an adaptive cognitive assessment and training system, in accordance with certain aspects of the present disclosure.
Figure 5A:
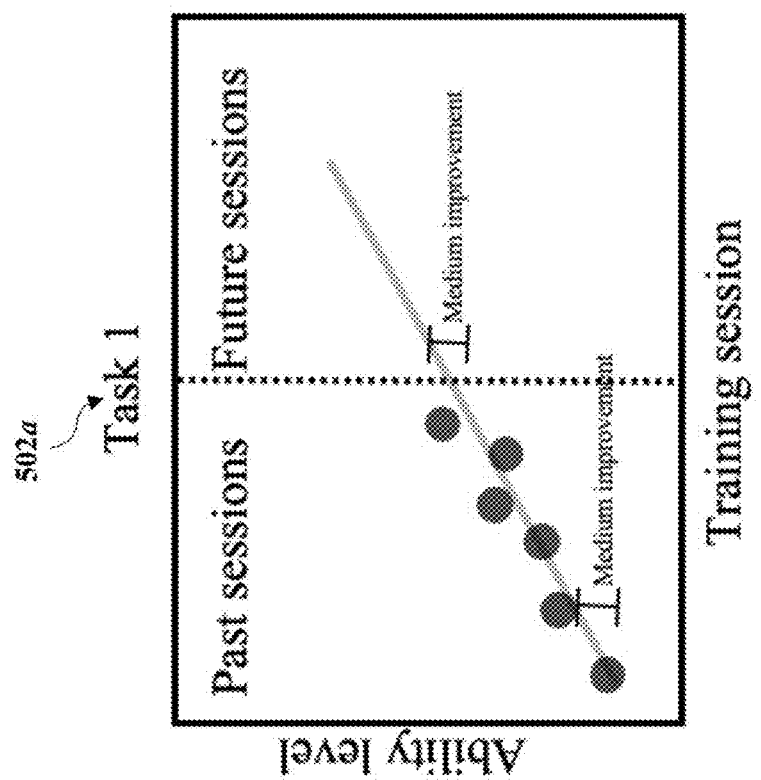
Figure 5D:
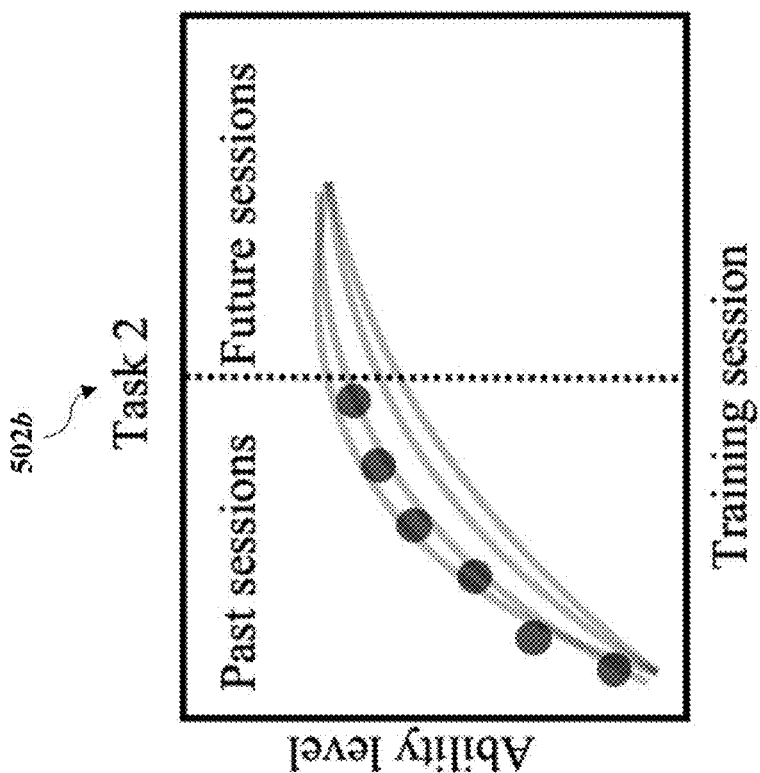
Figure 5C:
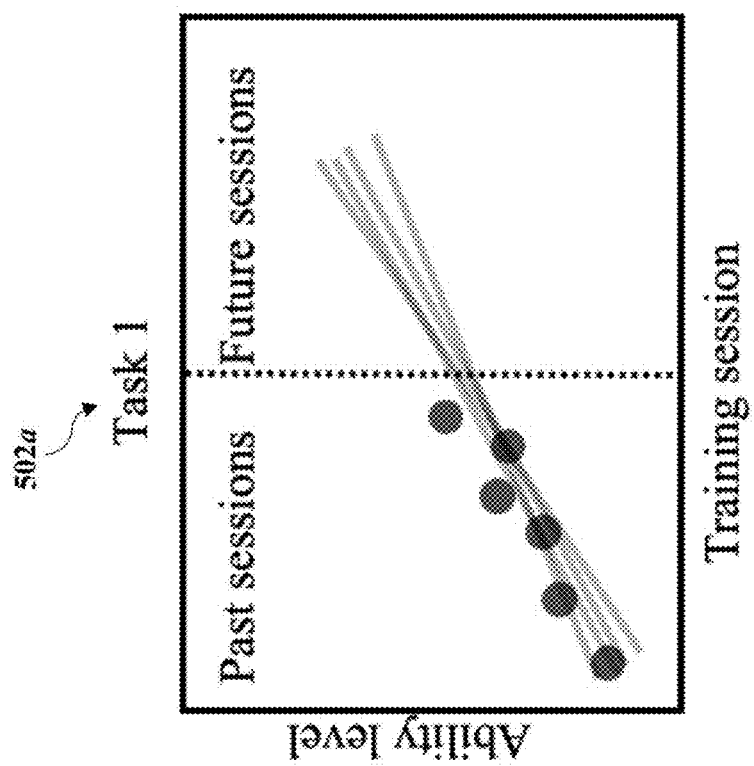

FIGS. 5A-5D are graphical diagrams of user assessment data and statistical analyses within an adaptive cognitive assessment and training system (e.g., adaptive cognitive assessment and training system 200 of FIG. 2). In accordance with certain aspects of the present disclosure, the adaptive cognitive assessment and training system may be configured to analyze user performance data for two or more types of cognitive training tasks across two or more past sessions of a computerized cognitive training regimen. As shown in FIGS. 5A and 5B, the adaptive cognitive assessment and training system may be configured to measure user performance data for a first cognitive training task 502a and a second cognitive training task 502b presented to a user during a training session of a computerized cognitive training regimen. In accordance with certain aspects of the present disclosure, first cognitive training task 502a may be associated with a first cognitive domain and second cognitive training task 502b may be associated with a second cognitive domain. The adaptive cognitive assessment and training system may be configured to receive and process the user input data for a computerized cognitive training session to determine a quantified measure of cognitive ability/skill of a user for first cognitive training task 502a and a quantified measure of cognitive ability/skill of the user associated with second cognitive training task 502b. The adaptive cognitive assessment and training system may be configured to analyze the quantified measure of cognitive ability across two or more past sessions of the computerized cognitive training regimen to determine an incremental degree of improvement in cognitive ability of the user between each of the two or more past sessions on a per task basis. As shown in FIGS. 5C and 5D, the adaptive cognitive assessment and training system may be configured to analyze the quantified measure of cognitive ability across two or more past sessions of the computerized cognitive training regimen on a per task basis according to the cognitive assessment model in order to predict an expected or relative value to a user of performing first cognitive training task 502a or second cognitive training task 502b in a future training session of the computerized cognitive training regimen.

Figure 6:
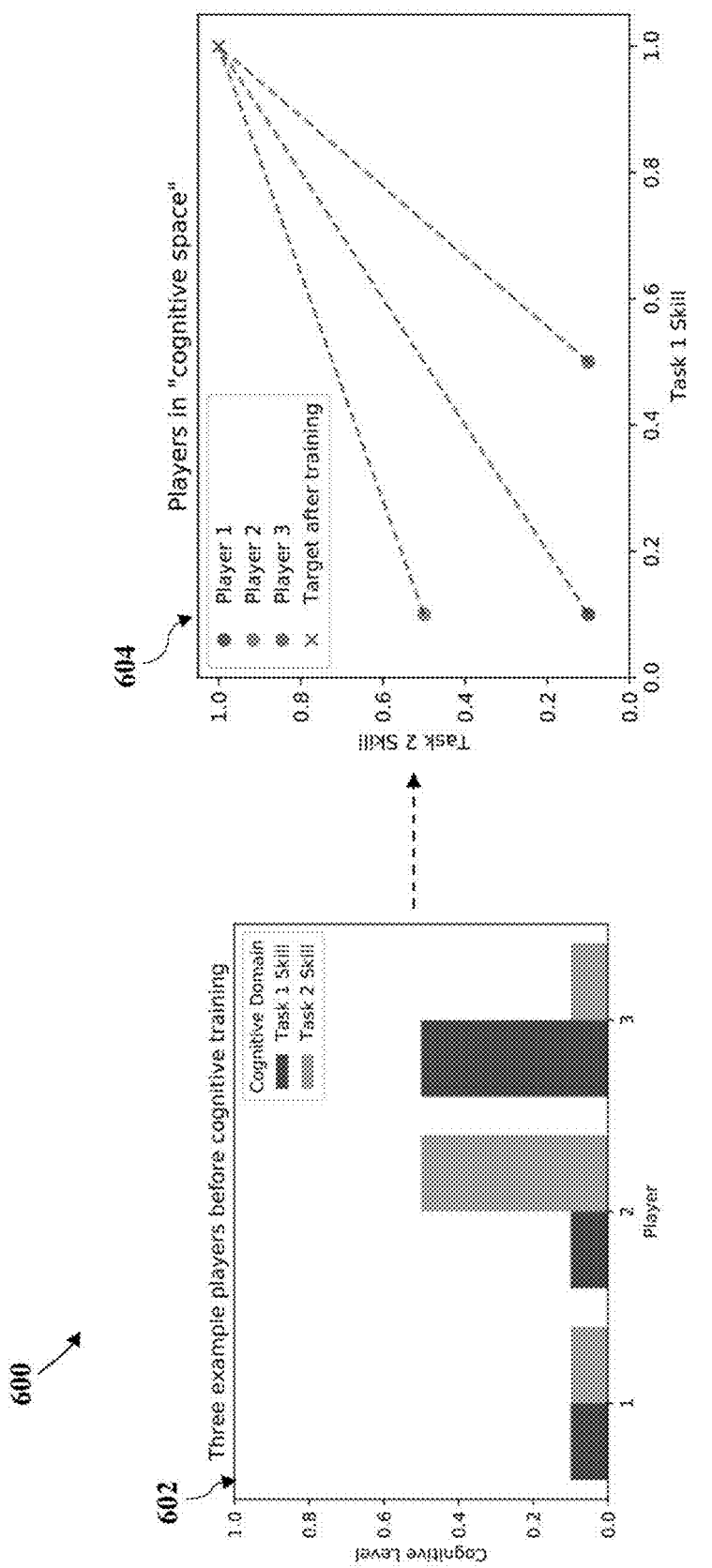
FIG. 6 is a graphical diagram of user assessment data and target performance analysis within an adaptive cognitive assessment and training system, in accordance with certain aspects of the present disclosure.

Referring now to FIG. 6, a graphical diagram 600 of baseline cognitive assessment data graph 602 and a cognitive training analysis plot 604 within an adaptive cognitive assessment and training system (e.g., adaptive cognitive assessment and training system 200 of FIG. 2). In accordance with certain aspects of the present disclosure, a cognitive assessment data graph 602 may comprise a baseline measure of a cognitive level for a first cognitive domain associated with a Task 1 skill and a second cognitive domain associated with a Task 2 skill for each of Player 1, Player 2, and Player 3. In accordance with certain aspects of the present disclosure, Player 1, Player 2, and Player 3 may comprise a user cohort in a cognitive assessment model. In accordance with certain embodiments, each user may complete a computerized cognitive assessment comprising a first cognitive training task, Task 1, and a second cognitive training task, Task 2. In accordance with various embodiments, Task 1 may comprise one or more CSIs configured to target one or more skills associated with a first cognitive domain (e.g., attention) and Task 2 may comprise one or more CSIs configured to target one or more skills associated with a second cognitive domain (e.g., memory). In accordance with various aspects of the present disclosure, the adaptive cognitive assessment and training system is configured to collect and process user performance data within the computerized cognitive assessment and analyze the user performance data to quantify a cognitive skill level for the user on a per task basis. As shown in FIG. 6, for example, a cognitive assessment for Player 1 determined a baseline cognitive skill level of 0.1 for Player 1 in a cognitive domain associated with the Task 1 skill and a baseline cognitive skill level of 0.1 for Player 1 in a cognitive domain associated with the Task 2 skill; a cognitive assessment for Player 2 determined a baseline cognitive skill level of 0.1 for Player 2 in a cognitive domain associated with the Task 1 skill and a baseline cognitive skill level of 0.5 for Player 2 in a cognitive domain associated with the Task 2 skill; and a cognitive assessment for Player 3 determined a baseline cognitive skill level of 0.5 for Player 3 in a cognitive domain associated with the Task 1 skill and a baseline cognitive skill level of 0.1 for Player 3 in a cognitive domain associated with the Task 2 skill. In certain embodiments, the adaptive cognitive assessment and training system may analyze the baseline cognitive assessment data according to an adaptive cognitive training framework to model a personalized cognitive training regimen for each of Player 1, Player 2, and Player 3. As shown in cognitive training analysis plot 604, the adaptive cognitive assessment and training system may analyze an expected trajectory of improvement for each of Player 1, Player 2, and Player 3 from their respective baseline cognitive skill levels to a target or maximal skill level (e.g., 1.0).

Figure 7:
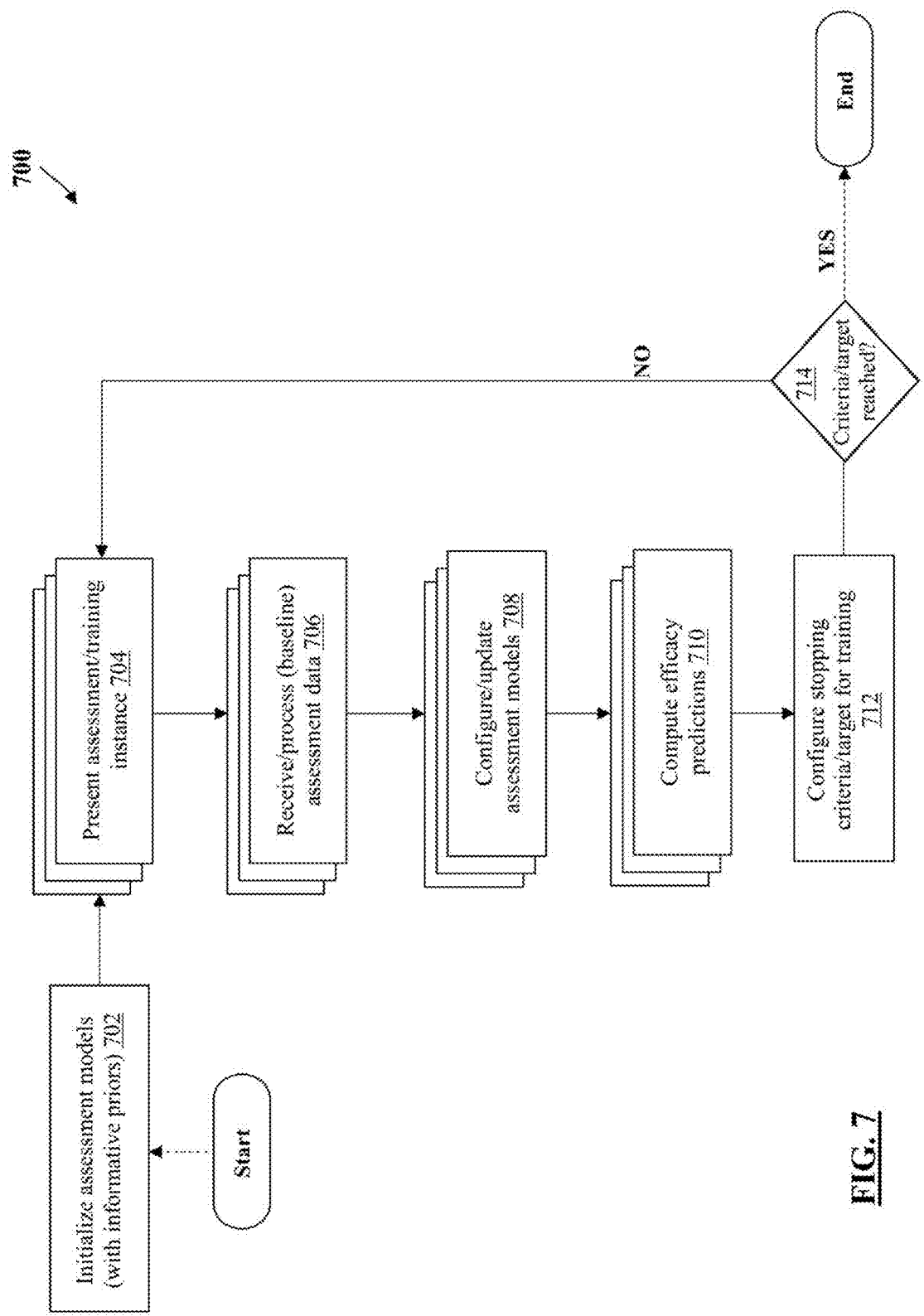
FIG. 7 is a functional block diagram of a routine for performing a user assessment within an adaptive cognitive assessment and training system, in accordance with certain aspects of the present disclosure.

Referring now to FIG. 7, a functional block diagram of a routine 700 for performing a user assessment within an adaptive cognitive assessment and training system is shown. In accordance with certain aspects of the present disclosure, routine 700 may be implemented in, or otherwise embodied as a component of, adaptive cognitive assessment and training system 200 (as shown and described in FIG. 2). In accordance with certain aspects of the present disclosure, routine 700 comprises one or more process steps and/or system operations for computing efficacy predictions for a user of a computerized cognitive training regimen and configuring or assessing one or more stopping criteria or training target for the computerized cognitive training regimen that is personalized to the user according to a cognitive assessment model. In accordance with certain aspects of the present disclosure, routine 700 is configured to solve the technical problem of determining a number of instances of a computerized cognitive training program to be presented to a user within a cognitive training regimen being personalized to a user and/or determining a stopping criterion for a cognitive training regimen being personalized to a user according to a cognitive assessment model. In accordance with certain aspects of the present disclosure, routine 700 may be initiated by an application server of the adaptive cognitive assessment and training system by performing one or more operations for initializing a cognitive assessment model comprising a plurality of informative prior cognitive assessment data being retrieved from an application database (Step 702). Routine 700 may proceed by performing one or more operations for presenting an instance of a computerized cognitive assessment/training program at a user interface of an end user device (Step 704). In accordance with various embodiments, the end user device is associated with an end user comprising an individual participating in the computerized cognitive training regimen. The instance of the computerized cognitive assessment/training program may be configured to present a plurality of CSIs at a user interface of an end user device, wherein the plurality of CSIs is configured as computerized cognitive assessment or training tasks configured to elicit an expected/desired stimulus-response pattern or protocol from the user at the end user device. The instance of the computerized cognitive assessment/training program may be configured to receive a plurality of user-generated inputs at the user interface of the end user device in response to presenting the plurality of CSIs. Routine 700 may proceed by performing one or more operations for receiving the plurality of user-generated inputs and processing the user-generated inputs as baseline/assessment data associated with the instance of the computerized cognitive assessment/training program (Step 706). Routine 700 may proceed by performing one or more operations for configuring and/or updating at least one assessment model for the computerized cognitive assessment/training regimen according to the baseline/assessment data (Step 708). Upon configuring/updating the at least one assessment model for the computerized cognitive assessment/training regimen according to the baseline/assessment data, routine 700 may proceed by computing one or more efficacy predictions for the computerized cognitive training regimen being personalized to the user (Step 710). In accordance with various aspects of the present disclosure, the one or more efficacy predictions may comprise a predicted measure of improvement in user performance of one or more computerized cognitive training tasks across one or more subsequent instances of the computerized cognitive assessment/training program and/or a predicted measure of impact that each task or instance of the computerized cognitive training program will have in improving one or more cognitive skills of the user. Routine 700 may further comprise one or more operations for configuring stopping criteria and/or a training target for the computerized cognitive training regimen being personalized to the user (Step 712). In certain embodiments, the stopping criteria or training target may comprise an estimated number of instances of the computerized cognitive training program until the user achieves a predetermined level of improvement at one or more cognitive skills. In certain embodiments, the stopping criteria or training target may comprise a minimum degree of user improvement between subsequent instances of the computerized cognitive training regimen. Routine 700 may proceed by executing one or more steps for evaluating the plurality of user-generated inputs in response to the plurality of CSIs to determine whether the stopping criteria or training target for the computerized cognitive training program has been reached (Step 714). If NO, routine 700 proceeds by configuring the next successive instance of the computerized cognitive assessment/training program and presenting the assessment/training instance at the user interface of the end user device in accordance with Step 704. In such cases, routine 700 is configured to repeat the operations for Steps 704-714. If YES, routine 700 is concluded and the data/model updates generated pursuant to routine 700 are stored in the application database.

Figure 8:
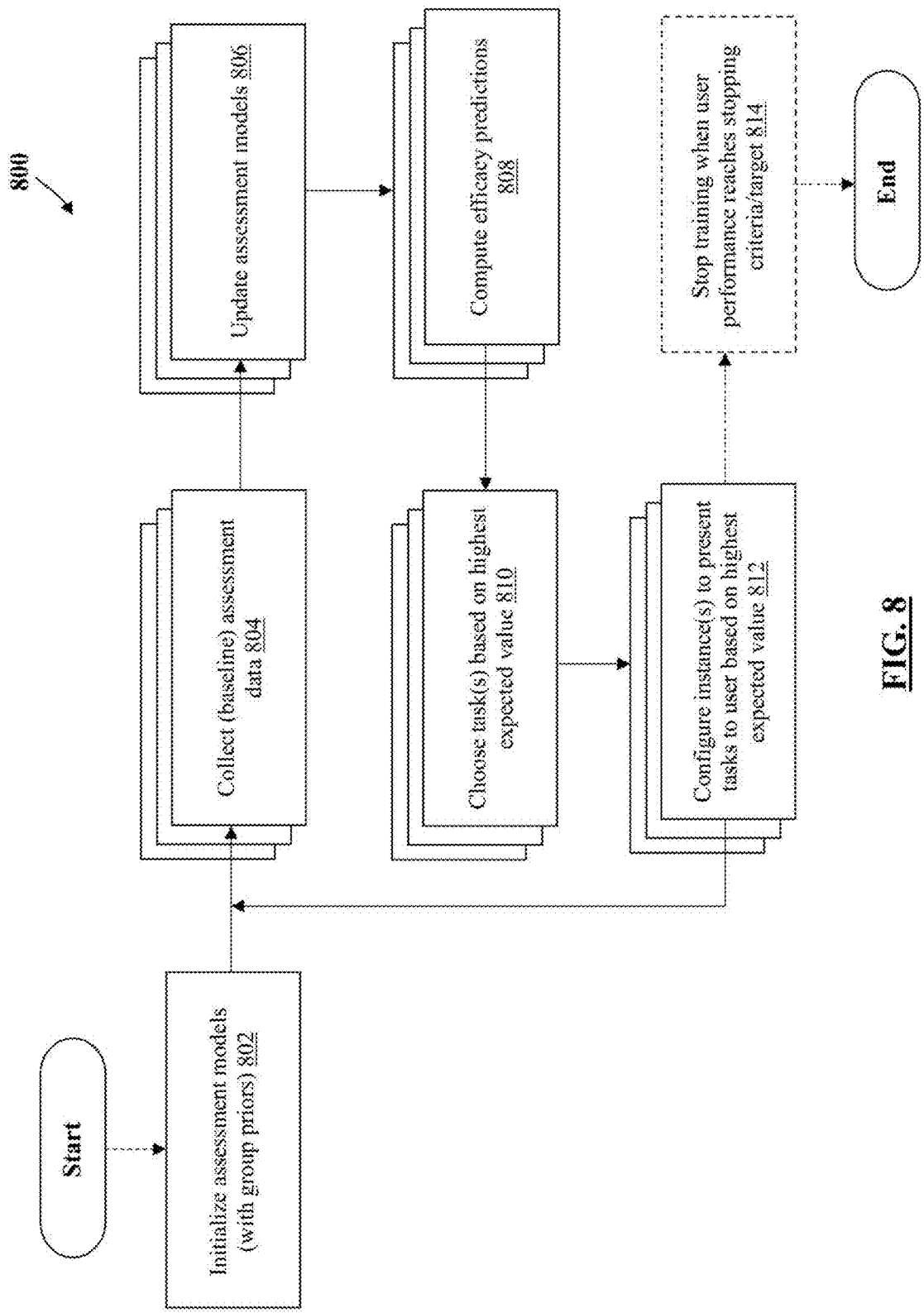
FIG. 8 is a functional block diagram of a routine for configuring a training instance within an adaptive cognitive assessment and training system, in accordance with certain aspects of the present disclosure.

Referring now to FIG. 8, a functional block diagram of a routine 800 for configuring an instance of a training session within an adaptive cognitive assessment and training system is shown. In accordance with certain aspects of the present disclosure, routine 800 may be implemented in, or otherwise embodied as a component of, adaptive cognitive assessment and training system 200 (as shown and described in FIG. 2). In certain embodiments, routine 800 may be sequential or successive to one or more steps of routine 700 (as shown and described in FIG. 7) and/or may comprise one or more sub-steps or sub-routines of routine 700. In accordance with certain aspects of the present disclosure, routine 800 comprises one or more process steps and/or system operations for adaptively/dynamically configuring one or more graphical user interface elements, difficulty level, user prompt, response-deadline and/or CSIs for one or more computerized cognitive training tasks within a computerized cognitive training program. To wit, routine 800 may be configured to continuously optimize/improve the efficacy and/or training efficiency of successive training sessions within a computerized cognitive training regimen.

In accordance with certain embodiments, routine 800 may be initiated to adaptively/dynamically configure one or more computerized cognitive training tasks by executing one or more operations to initialize one or more cognitive assessment models with group priors (Step 802). In accordance with certain aspects of the disclosure, a cognitive assessment model may comprise the cognitive assessment model as described in FIGS. 3A-3F, 4A-4D, 5A-5D and 6, above. In certain embodiments, routine 800 may proceed by executing one or more operations for collecting, within a session instance of a computerized cognitive training program, baseline cognitive assessment data for a user within a computerized cognitive training regimen (Step 804). Baseline cognitive assessment data may comprise a plurality of user-generated inputs received in response to a plurality of user prompts comprising one or more cognitive training tasks presented within a session instance of the computerized cognitive training program. Routine 800 may proceed by executing one or more operations for processing the baseline cognitive assessment data from Step 804 to update one or more cognitive assessment models for the user of the computerized cognitive training regimen (Step 806) (e.g., the cognitive assessment model for the user as defined/determine in routine 700). In certain embodiments, routine 800 may proceed by executing one or more operations for the processing the baseline assessment dataset (as collected pursuant to Step 804) according to the updated cognitive assessment model (as determined pursuant to Step 806) to compute one or more efficacy predictions for one or more therapeutically active CSIs/cognitive training tasks within the computerized cognitive training program (Step 808). In certain embodiments, routine 800 may proceed by executing one or more operations for selecting/determining one or more therapeutically active CSIs/cognitive training tasks having the highest cognitive training value to the user of the computerized cognitive training program (Step 810). In certain embodiments, Step 810 the one or more operations for selecting/determining one or more therapeutically active CSIs/cognitive training tasks having the highest cognitive training value to the user of the computerized cognitive training program may comprise operations for calculating an argmax for the cognitive training tasks having the highest efficacy/value to the user. In accordance with certain embodiments, an argmax for a cognitive training task "T" may be calculated according to:

$$T = \mathrm{argmax}(T1_v, T2_v, \ldots)$$

where $$Tn_v = (Tn_{x+1} - Tn_x)/Tn_{sd\ pooled}$$

Step 810 may additionally comprise one or more steps or operations for selection or configuring one or more graphical user interface elements, task difficulty level, cognitive engine (or combination of cognitive engines), and/or response-deadline procedure for the one or more therapeutically active CSIs/cognitive training tasks having the highest cognitive training value to the user of the computerized cognitive training program. Routine 800 may proceed further by executing one or more operations for configuring a subsequent instance of the computerized cognitive training program to render/present the modified/configured CSIs and/or cognitive training tasks having the highest expected value to the user of the computerized cognitive training program, based on the output of Step 810, within a successive session of the computerized cognitive training regimen (Step 812). In certain embodiments, routine 800 may proceed by executing one or more operations for determining whether the user performance data is reflective of a target cognitive performance level, and/or satisfies one or more stopping criteria, for the user within the computerized cognitive training regimen (Step 814). Step 814 may further comprise one or more steps or operations for ending a session of the computerized cognitive training program and/or terminating the computerized cognitive training regimen in response to determining the user has reached the target cognitive performance level and/or satisfied the one or more stopping criteria for the computerized cognitive training regimen. In certain embodiments, routine 800 may be configured to continuously execute Steps 804-812 across successive instances/sessions of the computerized cognitive training program until the output of Step 814 is indicative of the user having reached the target cognitive performance level and/or satisfied the one or more stopping criteria.

Figure 9:
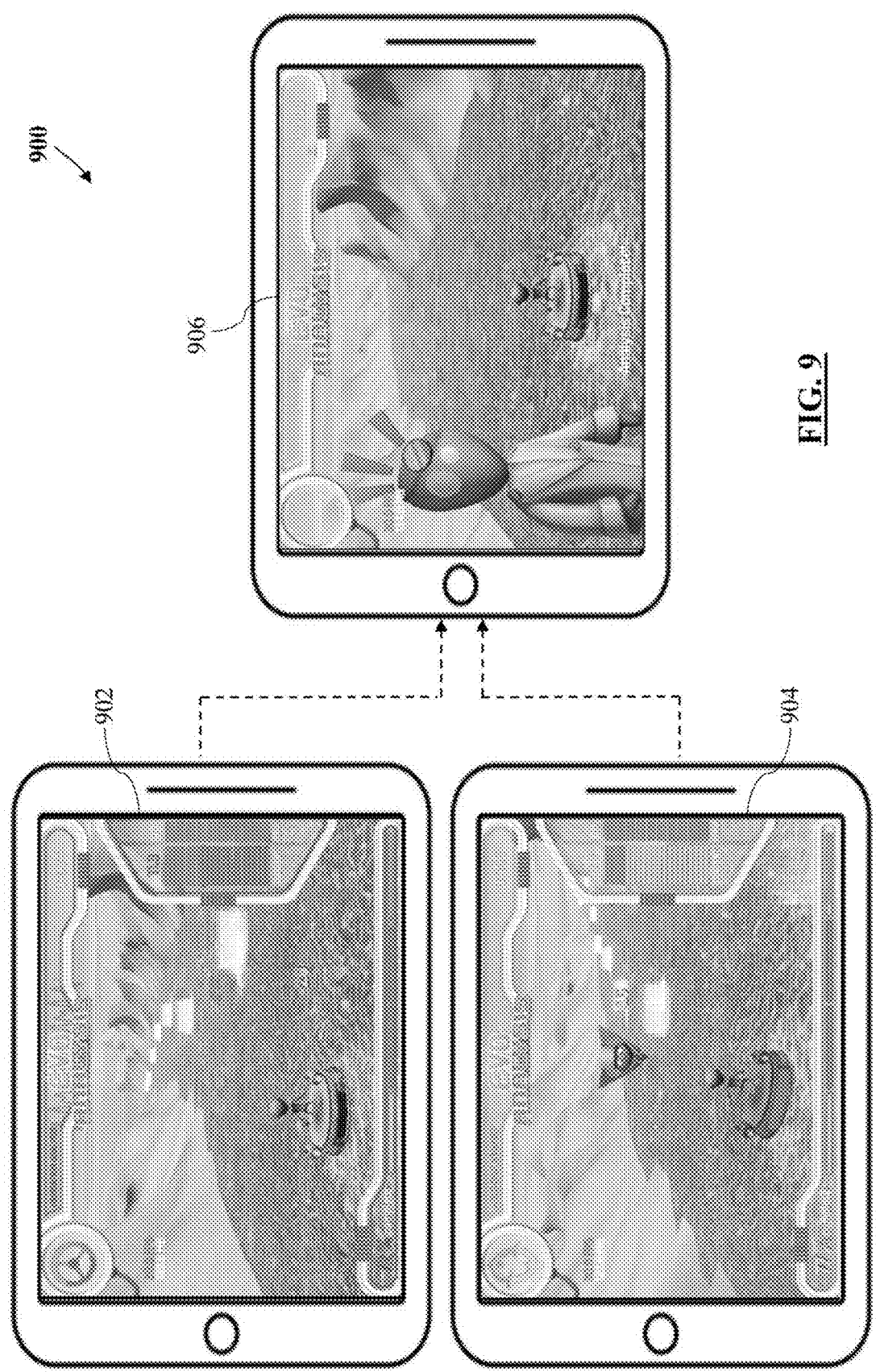
FIG. 9 is a functional diagram of a graphical user interface within an adaptive cognitive assessment and training system, in accordance with certain aspects of the present disclosure.

Referring now to FIG. 9, a functional diagram of graphical user interface screens of a computerized cognitive assessment 900 is shown. Computerized cognitive assessment 900 may be embodied within an adaptive cognitive assessment and training system; for example, adaptive cognitive assessment and training system 200 (as shown and described in FIG. 2). In accordance with certain aspects of the present disclosure, computerized cognitive assessment 900 is configured to assess the proficiency of a user of the adaptive cognitive assessment and training system (e.g., user 222 of FIG. 2) in one or more cognitive skills/domains. An instance of computerized cognitive assessment 900 may comprise one or more of user interface screens 902, 904 and 906. In accordance with certain embodiments, user interface screens 902 and 904 may be configured to render/present one or more CSIs associated with one or more computerized cognitive training tasks. In accordance with various embodiments, the one or more computerized cognitive training tasks are configured to present a plurality of user prompts configured to elicit a targeted stimulus-response pattern from the user. In accordance with various aspects of the present disclosure, a cognitive training engine is configured to render user interface screens 902 and 904 and process user-generated inputs in response thereto. The cognitive training engine may comprise comprising a plurality of encapsulated software functions comprising one or more algorithm for rendering, presenting and/or processing user-generated data according to one or more clinically validated stimulus-response patterns designed to target neural systems of the user (e.g., cognitive training engine 206 of FIG. 2). In certain embodiments, the one or more CSIs may comprise one or more components, prompts and/or graphical elements of a computerized cognitive training task configured to elicit a targeted stimulus-response pattern from the user within an instance of computerized cognitive assessment 900.

In certain embodiments, user interface screen 902 may be configured to render/present a first type of computerized task (e.g., a visuo-motor tracking task/navigation task) to assess user proficiency in a first cognitive skill/domain (e.g., focus) and user interface screen 904 may be configured to render/present a second type of computerized task (e.g., target discrimination) to assess user proficiency in a second cognitive skill/domain (e.g., attention). Computerized cognitive assessment 900 may be configured to continuously receive and process user-generated inputs comprising user responses to the cognitive tasks presented in user interface screen 902 and user interface screen 904. In various embodiments, computerized cognitive assessment 900 is configured to present the cognitive tasks to the user via user interface screen 902 and user interface screen 904 until sufficient user response data has been collected to perform a baseline cognitive assessment of the user's proficiency in the first cognitive skill/domain and the second cognitive skill/domain. Computerized cognitive assessment 900 may be configured to determine whether sufficient user response data has been received according to one or more static assessment criteria (e.g., task duration or number of user responses received) and/or adaptive procedures (e.g., task duration during which the user was applying effortful engagement or number of user responses received which conform to a designated stimulus-response pattern). In accordance with various aspects of the present disclosure, computerized cognitive assessment 900 may be configured to determine whether sufficient user response data has been received according to a cognitive assessment model. Upon determining that sufficient user response data has been received, and/or reaching some other stopping criteria, computerized cognitive assessment 900 may be configured to render/present user interface screen 906 at the graphical user interface to indicate that a session for computerized cognitive assessment 900 has ended.

Figure 10:
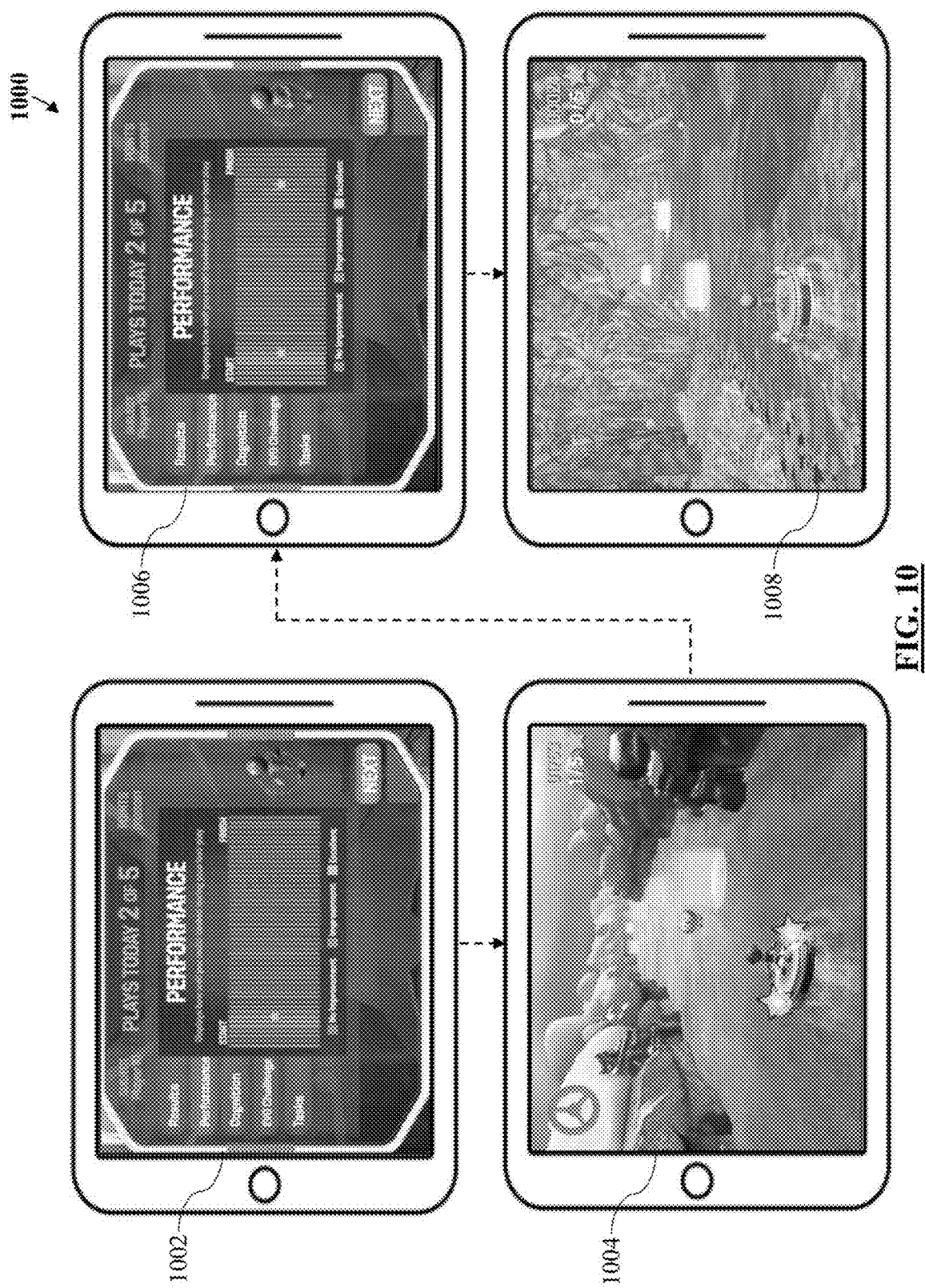
FIG. 10 is a functional diagram of a graphical user interface within an adaptive cognitive assessment and training system, in accordance with certain aspects of the present disclosure.

Referring now to FIG. 10, a functional diagram of graphical user interface screens of a computerized cognitive training program 1000 within an adaptive cognitive assessment and training system is shown. In accordance with certain aspects of the present disclosure, computerized cognitive training program 1000 may be embodied within an adaptive cognitive assessment and training system; for example, adaptive cognitive assessment and training system 200 (as shown and described in FIG. 2). Computerized cognitive training program 1000 may be configured to render/present one or more cognitive training tasks at a graphical user interface configured to elicit a targeted stimulus-response pattern from a user. In accordance with certain embodiments, the targeted stimulus-response pattern comprises one or more therapeutically active computerized tasks configured to train/improve the proficiency/skills of the user in one or more cognitive domains. One or more instances of computerized cognitive training program 1000 may comprise one or more of user interface screens 1002, 1004, 1006 and 1008. In accordance with certain aspects of the present disclosure, user interface screens 1002 and 1004 comprise an instance of a first session of computerized cognitive training program 1000 and user interface screens 1006 and 1008 comprise an instance of a second or subsequent session of computerized cognitive training program 1000. In accordance with various embodiments, a first session of computerized cognitive training program 1000 is configured to render/present one or more cognitive training tasks having the highest predicted efficacy/impact on the cognitive skills of the user based on the output of computerized cognitive assessment 900 (as shown in FIG. 9). User interface screens 1002 and 1006 may be configured to render/present a quantified graphical representation of a user's current cognitive performance level (i.e., proficiency of cognitive skill) for the cognitive training tasks based on the output of computerized cognitive assessment 900 and/or one or more prior sessions of computerized cognitive training program 1000.

In accordance with certain aspects of the present disclosure, the adaptive cognitive assessment and training system may be configured to initialize an instance of computerized cognitive training program 1000 comprising a training session for the user. Computerized cognitive training program 1000 may be configured to render user interface screen 1002 to display a current performance/progress level of the user for the computerized cognitive training regimen. The adaptive cognitive assessment and training system may be further configured to compute efficacy predictions for the cognitive training tasks based on the output from the cognitive assessment model to determine the task(s) having the highest expected value to the user (i.e., task(s) with the greatest expected impact on the user's cognitive skills). Computerized cognitive training program 1000 may be configured to render user interface screen 1004 comprising an instance of a training session in which one or more CSIs and/or graphical elements for the cognitive training tasks are modified and/or configured according to the efficacy predictions. In accordance with various embodiments, computerized cognitive training program 1000 may collect user performance data comprising user-generated inputs received in response to the cognitive training tasks presented/rendered during the training session comprising user interface screen 1004. In accordance with various aspects of the present disclosure, computerized cognitive training program 1000 is configured to process the user performance data to determine an updated performance level for the user and render/present a quantified graphical representation of the updated performance level via user interface screen 1006. In accordance with certain embodiments, the adaptive cognitive assessment and training system may be further configured to process the user performance data according to the cognitive assessment model (e.g., the cognitive assessment model as described in FIGS. 3A-3F, 4A-4D, 5A-5D and 6) to determine an updated cognitive assessment model for computerized cognitive training program 1000 and compute an updated efficacy prediction for the next successive session of computerized cognitive training program 1000. Computerized cognitive training program 1000 may be configured to further modify and/or configure the CSIs and/or graphical elements of computerized cognitive training program 1000 according to the updated efficacy prediction and render/present the cognitive training tasks having the highest expected value to the user in the next successive training session via user interface screen 1008. In certain embodiments, computerized cognitive training program 1000 is configured to collect and process user performance data for each successive training session until the user's performance level (i.e., proficiency of cognitive skill) reaches a target level and/or some other stopping criteria has been reached (e.g., maximum number of training instances or minimum change in performance level between training sessions). In accordance with certain embodiments, computerized cognitive training program 1000 may be configured as an interactive video game in which the one or more cognitive training tasks are incorporated as gameplay tasks associated with progression in the game. In certain embodiments, task utility may be continuous and may be integrated into a reward loop of the interactive video game. In certain embodiments, computerized cognitive training program 1000 may be configured to modify/adapt the configuration/presentation of game rewards according to expected efficacy of the one or more cognitive training tasks. A choice function within the interactive video game may be configured/modified to satisfy both gameplay objectives and one or more cognitive therapy objectives. In certain embodiments, game progression may be functionally linked to proficiency of cognitive assessment functions and/or cognitive performance rather than task completion.

Figure 11:
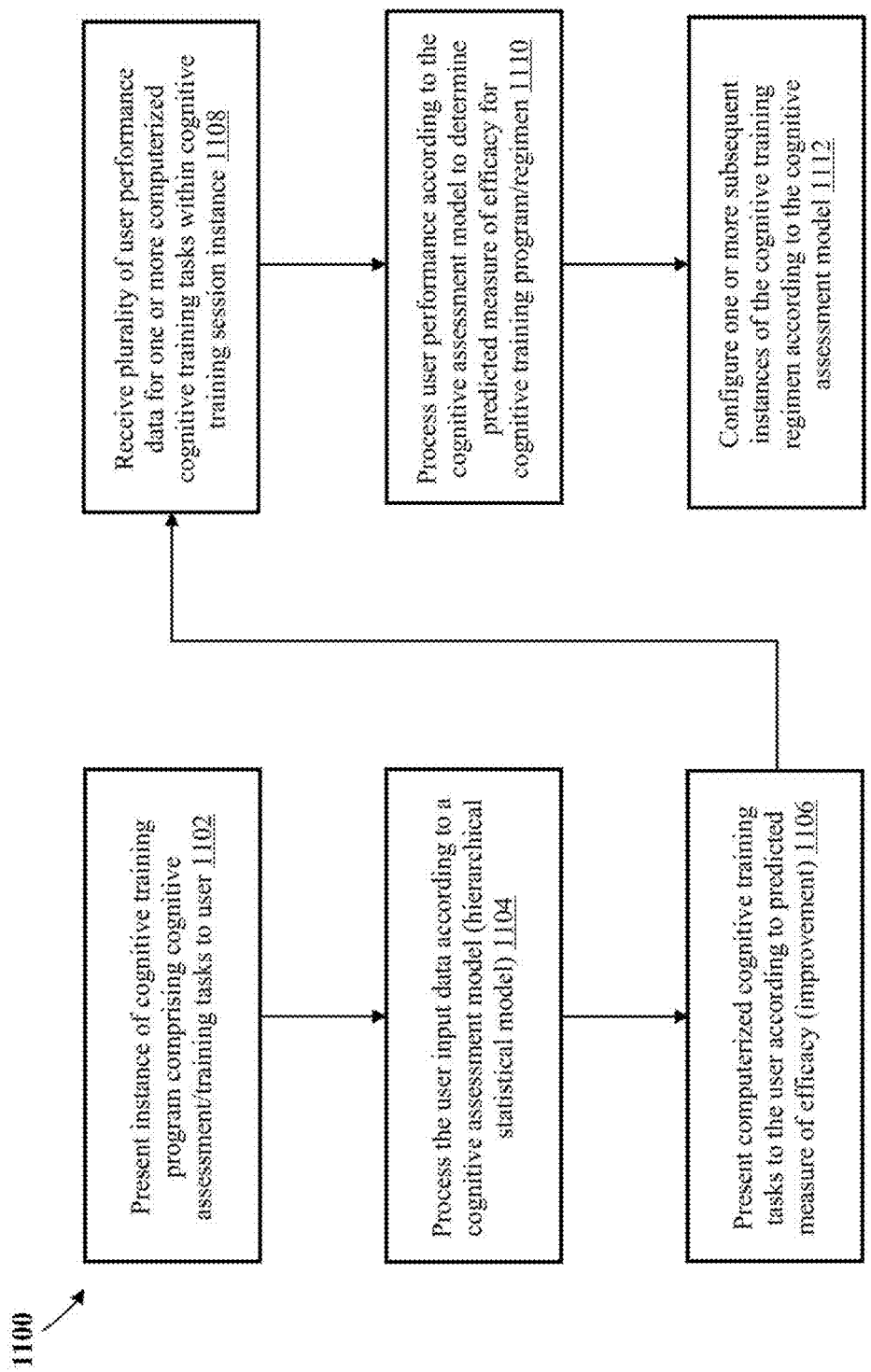
FIG. 11 is a process flow diagram of an adaptive cognitive assessment and training method, in accordance with certain aspects of the present disclosure.

Referring now to FIG. 11, a process flow diagram of an adaptive cognitive assessment and training method 1100 is shown. According to certain aspects of the present disclosure, method 1100 may comprise one or more of process steps 1102-1112. In certain embodiments, method 1100 may be implemented, in whole or in part, within adaptive cognitive assessment and training system 200 (as shown and described in FIG. 2). In certain embodiments, method 1100 may be embodied within one or more aspects of routine 700 and/or routine 800 (as shown in FIGS. 7-8). In accordance with certain aspects of the present disclosure, method 1100 may be initiated by presenting an instance of cognitive training program comprising cognitive assessment/training tasks to user (Step 1102). Method 1100 may proceed by processing the user input data according to a cognitive assessment model (e.g., the cognitive assessment model as described in FIGS. 3A-3F, 4A-4D, 5A-5D and 6) (Step 1104). In accordance with certain embodiments, method 100 may proceed by modifying and/or configuring the computerized cognitive training tasks according to predicted measure of efficacy (i.e., predicted degree of improvement in cognitive skill(s)) and presenting the computerized cognitive training tasks to a user of the computerized cognitive treatment program (Step 1106). Method 1100 may proceed by receiving a plurality of user-generated inputs comprising user performance data for one or more computerized cognitive training tasks presented within the cognitive training session instance (Step 1108). Method 1100 may proceed by processing the user performance data according to the cognitive assessment model to determine predicted measure of efficacy for cognitive training program/regimen (Step 1110). Method 1100 may proceed by configuring one or more subsequent instances of the cognitive training regimen according to the cognitive assessment model (Step 1112).

Figure 12:
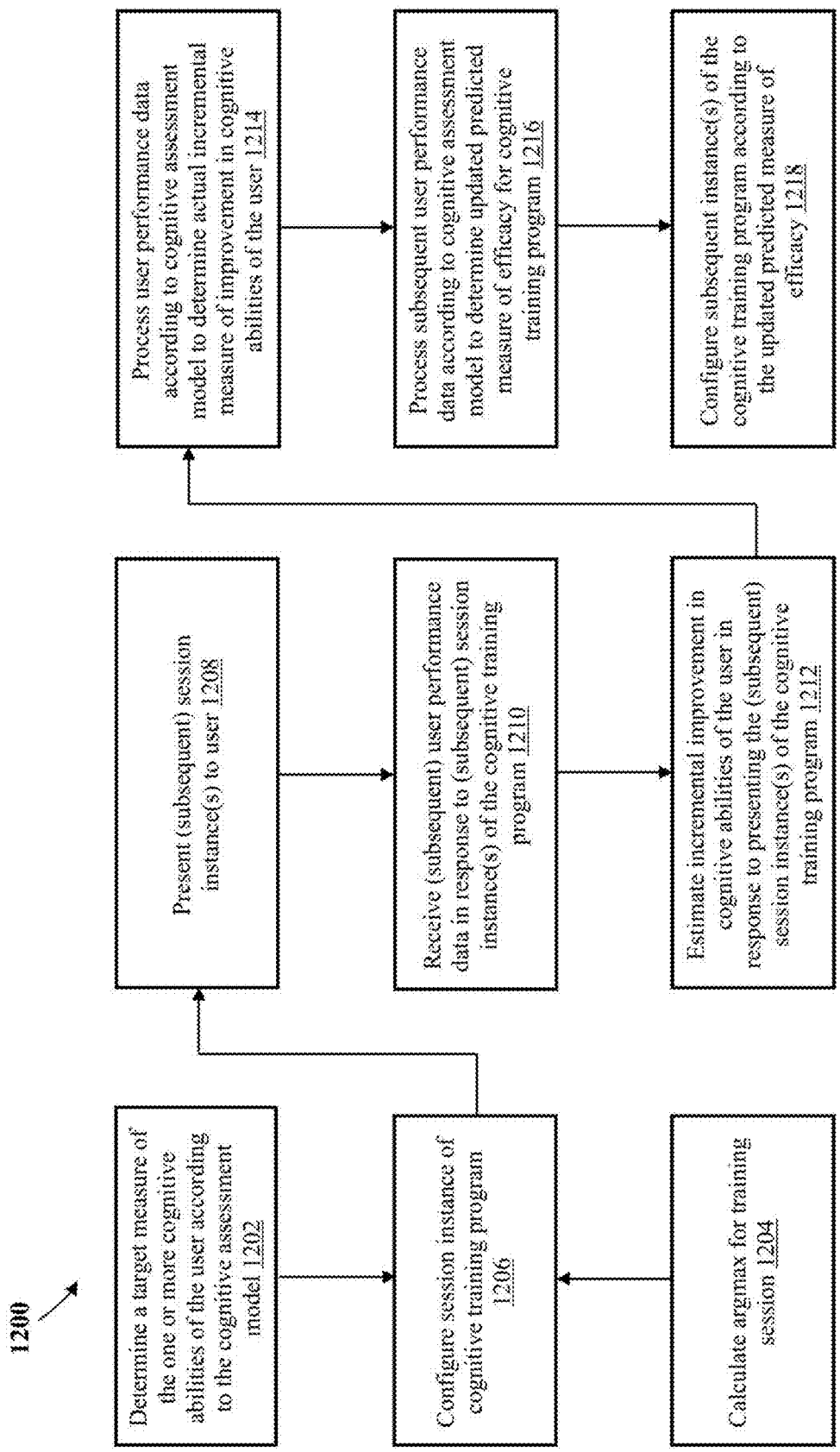
FIG. 12 is a process flow diagram of an adaptive cognitive assessment and training method, in accordance with certain aspects of the present disclosure.

Referring now to FIG. 12, a process flow diagram of an adaptive cognitive assessment and training method 1200 is shown. According to certain aspects of the present disclosure, method 1200 may comprise one or more of process steps 1202-1218. In certain embodiments, method 1200 may be implemented, in whole or in part, within adaptive cognitive assessment and training system 200 (as shown and described in FIG. 2). In certain embodiments, method 1200 may be embodied within one or more aspects of routine 700 and/or routine 800 (as shown in FIGS. 7-8) and may be sequential or successive to one or more steps of method 1100 (as shown and described in FIG. 11) and/or may comprise one or more sub-steps of method 1100. In accordance with certain aspects of the present disclosure, method 1200 may comprise one or more steps for determining a target measure of the one or more cognitive abilities of the user according to the cognitive assessment model (Step 1202) and calculating an argmax for a training session of the computerized cognitive training regimen (Step 1204). In certain embodiments, method 1200 may comprise one or more steps for configuring a session instance of the computerized cognitive training program (Step 1206). Method 1200 may proceed by executing one or more steps for presenting a current or subsequent session instance of the computerized cognitive training program to the user (Step 1208). Method 1200 may proceed by receiving user performance data in response to the session instance of the cognitive training regimen (Step 1210). Method 1200 may proceed by estimating an incremental improvement in cognitive abilities of the user in response to presenting the current or subsequent session instance of the computerized cognitive training program (Step 1212). Method 1200 may proceed by executing one or more steps for processing user performance data according to cognitive assessment model to determine an actual incremental measure of improvement in cognitive abilities of the user (Step 1214). In accordance with certain embodiments, method 1200 may proceed by executing one or more steps for processing subsequent user performance data according to cognitive assessment model to determine an updated predicted measure of efficacy for the cognitive training program (Step 1216). Method 1200 may conclude by executing on or more steps for configuring one or more subsequent instance(s) of the cognitive training regimen according to the updated predicted measure of efficacy (Step 1218).

As will be appreciated by one of skill in the art, the present invention may be embodied as a method (including, for example, a computer-implemented process, a business process, and/or any other process), apparatus (including, for example, a system, machine, device, computer program product, and/or the like), or a combination of the foregoing. Accordingly, embodiments of the present invention may take the form of an entirely hardware embodiment, an entirely software embodiment (including firmware, resident software, micro-code, and the like), or an embodiment combining software and hardware aspects that may generally be referred to herein as a "system." Furthermore, embodiments of the present invention may take the form of a computer program product on a computer-readable medium having computer-executable program code embodied in the medium.

Any suitable transitory or non-transitory computer readable medium may be utilized. The computer readable medium may be, for example but not limited to, an electronic, magnetic, optical, electromagnetic, infrared, or semiconductor system, apparatus, or device. More specific examples of the computer readable medium include, but are not limited to, the following: an electrical connection having one or more wires; a tangible storage medium such as a portable computer diskette, a hard disk, a random-access memory (RAM), a read-only memory (ROM), an erasable programmable read-only memory (EPROM or Flash memory), a compact disc read-only memory (CD-ROM), or other optical or magnetic storage device.

In the context of this document, a computer readable medium may be any medium that can contain, store, communicate, or transport the program for use by or in connection with the instruction execution system, apparatus, or device. The computer usable program code may be transmitted using any appropriate medium, including but not limited to the Internet, wireline, optical fiber cable, radio frequency (RF) signals, or other mediums.

Computer-executable program code for carrying out operations of embodiments of the present invention may be written in an object oriented, scripted or unscripted programming language such as Java, Perl, Smalltalk, C++, or the like. However, the computer program code for carrying out operations of embodiments of the present invention may also be written in conventional procedural programming languages, such as the "C" programming language or similar programming languages.

Embodiments of the present invention are described above with reference to flowchart illustrations and/or block diagrams of methods, apparatus (systems), and computer program products. It will be understood that each block of the flowchart illustrations and/or block diagrams, and/or combinations of blocks in the flowchart illustrations and/or block diagrams, can be implemented by computer-executable program code portions. These computer-executable program code portions may be provided to a processor of a general-purpose computer, special purpose computer, or other programmable data processing apparatus to produce a particular machine, such that the code portions, which execute via the processor of the computer or other programmable data processing apparatus, create mechanisms for implementing the functions/acts specified in the flowchart and/or block diagram block or blocks.

These computer-executable program code portions (i.e., computer-executable instructions) may also be stored in a computer-readable memory that can direct a computer or other programmable data processing apparatus to function in a particular manner, such that the code portions stored in the computer readable memory produce an article of manufacture including instruction mechanisms which implement the function/act specified in the flowchart and/or block diagram block(s). Computer-executable instructions may be in many forms, such as program modules, executed by one or more computers or other devices. Generally, program modules include routines, programs, objects, components, data structures, and the like that perform particular tasks or implement particular abstract data types. Typically, the functionality of the program modules may be combined or distributed as desired in various embodiments.

The computer-executable program code may also be loaded onto a computer or other programmable data processing apparatus to cause a series of operational phases to be performed on the computer or other programmable apparatus to produce a computer-implemented process such that the code portions which execute on the computer or other programmable apparatus provide phases for implementing the functions/acts specified in the flowchart and/or block diagram block(s). Alternatively, computer program implemented phases or acts may be combined with operator or human implemented phases or acts in order to carry out an embodiment of the invention.

As the phrases are used herein, a processor may be "operable to" or "configured to" perform a certain function in a variety of ways, including, for example, by having one or more general-purpose circuits perform the function by executing particular computer-executable program code embodied in computer-readable medium, and/or by having one or more application-specific circuits perform the function.

The terms "program" or "software" are used herein in a generic sense to refer to any type of computer code or set of computer-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." As used herein, the terms "right," "left," "top," "bottom," "upper," "lower," "inner" and "outer" designate directions in the drawings to which reference is made.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); and the like As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of" when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); and the like In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The present disclosure includes that contained in the appended claims as well as that of the foregoing description. Although this invention has been described in its exemplary forms with a certain degree of particularity, it is understood that the present disclosure of has been made only by way of example and numerous changes in the details of construction and combination and arrangement of parts may be employed without departing from the spirit and scope of the invention.

What is claimed is:

1. A method for configuring a user interface within a computerized cognitive training regimen, comprising:

presenting, with a processor communicably engaged with a computing device, one or more instances of the computerized cognitive training regimen to a user, the computerized cognitive training regimen comprising two or more computerized cognitive training tasks presented via a display of the computing device, wherein a first task in the two or more computerized cognitive training tasks is configured to target a first cognitive ability of the user and a second task in the two or more computerized cognitive training tasks is configured to target a second cognitive ability of the user, wherein the computerized cognitive training regimen comprises an interactive video game in which the two or more computerized cognitive training tasks are gameplay tasks associated with a gameplay progression of the interactive video game, wherein each task in the two or more computerized cognitive training tasks comprises a set of computerized stimuli or interactions comprising dynamically rendered graphical elements rendered at a first graphical user interface screen of the interactive video game according to at least one response-deadline procedure;

receiving, with the processor via the computing device, a plurality of user input data in response to the two or more computerized cognitive training tasks, wherein the plurality of user input data comprises a plurality of sensor data derived from an interaction of the user with a sensor device in response to the set of computerized stimuli or interactions;

processing, with the processor, the plurality of user input data according to a cognitive assessment model to determine a quantified measure of the first cognitive ability of the user and the second cognitive ability of the user for each instance in the one or more instances of the computerized cognitive training regimen;

analyzing, with the processor, the first cognitive ability of the user and the second cognitive ability of the user for each instance in the one or more instances of the computerized cognitive training regimen to determine at least one gameplay progression criterion for the interactive video game;

processing, with the processor, the plurality of user input data according to the cognitive assessment model to determine a predicted measure of efficacy for each task in the two or more computerized cognitive training tasks;

configuring, with the processor, a subsequent graphical user interface screen of the interactive video game according to the quantified measure of the first cognitive ability of the user and the second cognitive ability of the user and the at least one gameplay progression criterion, wherein configuring the subsequent graphical user interface screen of the interactive video game comprises configuring or modifying a first set of computerized stimuli or interactions associated with a first task in the two or more computerized cognitive training tasks according to the predicted measure of efficacy, wherein configuring or modifying the first set of computerized stimuli or interactions comprises dynamically modifying at least one graphical element in the first set of computerized stimuli or interactions, wherein the at least one graphical element comprises a therapeutically active element configured to target the first cognitive ability of the user, wherein the predicted measure of efficacy comprises a predicted incremental measure of improvement in the first cognitive ability of the user and/or the second cognitive ability of the user; and presenting, with the processor via the display of the computing device, the subsequent graphical user interface screen of the interactive video game to the user.

2. The method of claim 1 further comprising determining, with the processor, a target measure of the first cognitive ability of the user and the second cognitive ability of the user according to the cognitive assessment model, wherein the target measure comprises an estimated asymptotic maximum or estimated marginal output value for the predicted incremental measure of improvement in the first cognitive ability of the user and the second cognitive ability of the user.

3. The method of claim 1 further comprising receiving, with the processor via the computing device, a subsequent plurality of user input data in response to presenting the subsequent graphical user interface screen of the interactive video game to the user.

4. The method of claim 3 further comprising estimating, with the processor, an incremental measure of improvement in the first cognitive ability of the user and the second cognitive ability of the user in response to presenting the subsequent graphical user interface screen of the interactive video game to the user.

5. The method of claim 4 further comprising processing, with the processor, the subsequent plurality of user input data according to the cognitive assessment model to determine an actual incremental measure of improvement in the first cognitive ability of the user and the second cognitive ability of the user.

6. The method of claim 5 further comprising processing, with the processor, the subsequent plurality of user input data according to the cognitive assessment model to determine an updated predicted measure of efficacy for the computerized cognitive training regimen.

7. The method of claim 6 further comprising configuring, with the processor, the subsequent graphical user interface screen of the interactive video game according to the updated predicted measure of efficacy.

8. The method of claim 1 wherein the predicted measure of efficacy comprises calculating an argmax for each task in the two or more computerized cognitive training tasks according to the cognitive assessment model.

9. The method of claim 8 further comprising configuring, with the processor, the subsequent graphical user interface screen of the interactive video game according to the calculated argmax.

10. A system for configuring a user interface within a computerized cognitive training regimen, comprising:

a user interface device comprising a display and an input device comprising at least one sensor;

a processor communicably engaged with the user interface device; and a non-transitory computer readable storage medium communicably engaged with the processor and encoded with processor-executable instructions that, when executed, cause the processor to perform one or more operations comprising:

presenting one or more instances of the computerized cognitive training regimen to a user, wherein each instance in the one or more instances comprises a graphical user interface configured to present two or more computerized cognitive training tasks via the display of the user interface device, wherein a first task in the two or more computerized cognitive training tasks is configured to target a first cognitive ability of the user and a second task in the two or more computerized cognitive training tasks is configured to target a second cognitive ability of the user, wherein the computerized cognitive training regimen comprises an interactive video game in which the two or more computerized cognitive training tasks are gameplay tasks associated with a gameplay progression of the interactive video game, wherein each task in the two or more computerized cognitive training tasks comprises a set of computerized stimuli or interactions comprising dynamically rendered graphical elements rendered at a first graphical user interface screen of the interactive video game according to at least one response-deadline procedure;

receiving a plurality of user input data in response to the two or more computerized cognitive training tasks, wherein the plurality of user input data comprises a plurality of sensor data derived from an interaction of the user with a sensor device in response to the set of computerized stimuli or interactions;

processing the plurality of user input data according to a cognitive assessment model to determine a quantified measure of the first cognitive ability of the user and the second cognitive ability of the user for each instance in the one or more instances of the computerized cognitive training regimen;

analyzing the first cognitive ability of the user and the second cognitive ability of the user for each instance in the one or more instances of the computerized cognitive training regimen to determine at least one gameplay progression criterion for the interactive video game;

processing the plurality of user input data according to the cognitive assessment model to determine a predicted measure of efficacy for each task in the two or more computerized cognitive training tasks;

configuring, with the processor, a subsequent graphical user interface screen of the interactive video game according to the quantified measure of the first cognitive ability of the user and the second cognitive ability of the user and the at least one gameplay progression criterion, wherein configuring the subsequent graphical user interface screen of the interactive video game comprises configuring or modifying a first set of computerized stimuli or interactions associated with a first task in the two or more computerized cognitive training tasks according to the predicted measure of efficacy, wherein configuring or modifying the first set of computerized stimuli or interactions comprises dynamically modifying at least one graphical element in the first set of computerized stimuli or interactions, wherein the at least one graphical element comprises a therapeutically active element configured to target the first cognitive ability of the user, wherein the predicted measure of efficacy comprises a predicted incremental measure of improvement in the first cognitive ability of the user and/or the second cognitive ability of the user; and presenting, via the display of the user interface device, the subsequent graphical user interface screen of the interactive video game to the user.

11. The system of claim 10 wherein the one or more operations further comprise estimating an incremental measure of improvement in the first cognitive ability of the user and the second cognitive ability of the user in response to presenting the subsequent graphical user interface screen of the interactive video game to the user.

12. The system of claim 11 wherein the one or more operations further comprise determining a target measure of the first cognitive ability of the user and the second cognitive ability of the user according to the cognitive assessment model, wherein the target measure comprises an asymptotic maximum or marginal output value for the incremental measure of improvement in the first cognitive ability of the user and the second cognitive ability of the user.

13. The system of claim 10 wherein the one or more operations further comprise receiving a subsequent plurality of user input data in response to presenting the subsequent graphical user interface screen of the interactive video game to the user.

14. The system of claim 13 wherein the one or more operations further comprise processing the subsequent plurality of user input data according to the cognitive assessment model to determine an actual incremental measure of improvement in the first cognitive ability of the user and the second cognitive ability of the user.

15. The system of claim 14 wherein the one or more operations further comprise processing the subsequent plurality of user input data according to the cognitive assessment model to determine an updated predicted measure of efficacy for the two or more computerized cognitive training tasks.

16. The system of claim 15 wherein the one or more operations further comprise configuring the subsequent graphical user interface screen of the interactive video game according to the updated predicted measure of efficacy.

17. The system of claim 10 wherein the one or more operations further comprise calculating an argmax for each task in the two or more computerized cognitive training tasks according to the cognitive assessment model.

18. The system of claim 17 wherein the one or more operations further comprise configuring the subsequent graphical user interface screen of the interactive video game according to the calculated argmax.

19. The system of claim 18 wherein the one or more operations further comprise modifying or configuring one or more interface elements of the subsequent graphical user interface screen of the interactive video game according to the argmax, wherein the one or more interface elements comprise at least one interface element for the two or more computerized cognitive training tasks.

20. A non-transitory computer-readable medium encoded with instructions for commanding one or more processors to execute operations for configuring a user interface within a computerized cognitive training regimen, the operations comprising:

presenting one or more instances of the computerized cognitive training regimen to a user via a display of a computing device, wherein the computerized cognitive training regimen comprises an interactive video game comprising two or more computerized cognitive training tasks, wherein the two or more computerized cognitive training tasks are gameplay tasks associated with a gameplay progression of the interactive video game, wherein a first task in the two or more computerized cognitive training tasks is configured to target a first cognitive ability of the user and a second task in the two or more computerized cognitive training tasks is configured to target a second cognitive ability of the user,
wherein each task in the two or more computerized cognitive training tasks comprises a set of computerized stimuli or interactions comprising dynamically rendered graphical elements rendered at a first graphical user interface screen of the interactive video game according to at least one response-deadline procedure;
receiving a plurality of user input data in response to the two or more computerized cognitive training tasks,
wherein the plurality of user input data comprises a plurality of sensor data derived from an interaction of the user with a sensor device in response to the set of computerized stimuli or interactions;
processing the plurality of user input data according to a cognitive assessment model to determine a quantified measure of the first cognitive ability of the user and the second cognitive ability of the user for each instance in the one or more instances of the computerized cognitive training regimen;
analyzing the first cognitive ability of the user and the second cognitive ability of the user for each instance in the one or more instances of the computerized cognitive training regimen to determine at least one gameplay progression criterion for the interactive video game;
processing the plurality of user input data according to the cognitive assessment model to determine a predicted measure of efficacy for each task in the two or more computerized cognitive training tasks;
configuring a subsequent graphical user interface screen of the interactive video game according to the quantified measure of the first cognitive ability of the user and the second cognitive ability of the user and the at least one gameplay progression criterion,
wherein configuring the subsequent graphical user interface screen of the interactive video game comprises configuring or modifying a first set of computerized stimuli or interactions associated with a first task in the two or more computerized cognitive training tasks according to the predicted measure of efficacy,
wherein configuring or modifying the first set of computerized stimuli or interactions comprises dynamically modifying at least one graphical element in the first set of computerized stimuli or interactions,
wherein the at least one graphical element comprises a therapeutically active element configured to target the first cognitive ability of the user,
wherein the predicted measure of efficacy comprises a predicted incremental measure of improvement in the first cognitive ability of the user and/or the second cognitive ability of the user; and
presenting the subsequent graphical user interface screen of the interactive video game to the user via the display of the computing device.

* * * * *